United States Patent [19]
Hirschberg et al.

[11] Patent Number: 5,541,095
[45] Date of Patent: Jul. 30, 1996

[54] GLYCOSAMINOGLYCAN SPECIFIC SULFOTRANSFERASES

[75] Inventors: Carlos B. Hirschberg, Worcester; Ariel Orellana, Shrewsbury, both of Mass.; Yasuhiro Hashimoto, Chiba, Japan; Stuart J. Swiedler, Oakland, Calif.; Zheng Wei, Fremont, Calif.; Masayuki Ishihara, Alameda, Calif.

[73] Assignee: University of Massachusetts Medical Center, Worcester, Mass.

[21] Appl. No.: 57,167

[22] Filed: Apr. 30, 1993

Related U.S. Application Data

[63] Continuation-in-part of Ser. No. 899,423, Jun. 16, 1992, abandoned.

[51] Int. Cl.$^6$ .......................... C12N 15/54; C12N 15/55; C12N 9/10; C12N 9/78
[52] U.S. Cl. .......................... 435/172.3; 435/69.1; 435/6; 435/193; 435/227; 435/228; 435/252.3; 435/240.2; 435/320.1; 536/23.1; 536/23.2; 536/23.4; 514/44
[58] Field of Search .......................... 435/69.1, 6, 172.3, 435/193, 227, 228, 252.3, 240.2, 320.1; 536/23.2, 231, 23.4; 514/44

[56] References Cited

U.S. PATENT DOCUMENTS 5,032,519   7/1991   Paulson et al. .......................... 435/193

OTHER PUBLICATIONS

Klagsbrun et al. 1991. Cell 67:229.
Kushe et al. 1991. Biochem. J. 275:151.
Pettersson et al. 1991. J. Biol. Chem 266:8044.
Rapraeger et al. 1991. Science 252:1705.
Roche et al. 199. Cell 67:1131.
Sakaguchi et al. 1991. J. Biol. Chem. 266:7270.
Yayon et al. 1991. Cell 64:841.
Lupa et al. 1990. Dev. Biol. 143:31.
Ogura et al. Biochemical and Biophysical Research Communications 166:1494.
Andersson et al. 1989. J. Biol. Chem. 264:8222.
Bame et al. 1989. J. Biol. Chem. 264:8059.
LeBaron et al. 1989. J. Biol. Chem. 264:7950.
Ogura et al. 1989. Biochemical and Biophysical Research Communications. 165:168.
Ostrowski et al. 1989. J. Biol. Chem. 264:15726.
WuDunn et al. 1989. Journal of Virology. 63:52.
Brandan et al. 1988. J. Biol. Chem. 263:2417.
Esko et al. 1988. Science. 241:1092.
LeBaron et al. 1988. J. Cell Biol. 160:945.
Lindahl et al in *Biology of Proteoglycans*.Wight et al., pp. 59, Academic Press, 1987.
Lindahl et al. TIBS. May 1986, pp. 221–225.
Lee et al. 1985. Proc. Natl. Acad. Sci. USA 82:6143.
Green et al. 1984. Proc. Natl. Acad. Sci. USA 81:5320.
Kanwar et al. 1984. 81:762.
Lindhal et al. 1984. J. Biol. Chem. 259:12368.
Yanagishita et al. 1984. J. Biol. Chem. 259:10270.
Kjellen et al. 1981. Proc. Natl. Acad. Sci. 78:537.
Fleischer et al. 1974. J. Biol. Chem. 249:5995.
Young, R. W. 1973. J. Cell Biol. 57:175.
Horwitz et al. 1968. J. Cell Biol. 38:358.
Kjellen et al., Adv. Exptl. Med. Biol. 312:107, 1992.
R. Sanchez–Lopes et al. "Structure–Function Relationships in the Collegenase Family Members Transin" J. Biol. Chem. 263(24) 11892–11899 (Aug. 1988).
K. J. Bame et al. J. Biol. Chem. 266(19) 12461–12468 (Jul. 1991).
L. Kjellen et al. Adv. Exp. Med. Biol. 313:107–111 (1992) –See Enclosed Abstract: Chemical. Absts. 118:75739.
U. Lindahl et al. J. Cell. Biochem. 48 Suppl. p. 139 (1992).
I. Petterson et al. J. Biol. Chem. 266(13) 8044–8049 (May 1991).
M. P. Deutscher (ed.) "Guide to Protein Purification" Meth. in Enzymology. 182: 602–613, 738–751 (1990).
S. C. Berger et al. (eds.) "Guide to Molecular Cloning Techniques" Meth. in Enzymology 152:393–399, 415–423, 432–447, 661–704 (1987).
A. Belyowsky et al. Nuc. Acids. Res. 17(8) 2919–2932 (Apr. 1989).

*Primary Examiner*—Robert A. Wax
*Assistant Examiner*—Rebecca Prouty
*Attorney, Agent, or Firm*—Fish & Richardson P.C.

[57] ABSTRACT

DNA encoding a polypeptide capable of catalyzing the deacetylation and sulfation of a glycosaminoglycan; production and isolation of recombinant and synthetic polypeptides capable of catalyzing the deacetylation, sulfation or both the deacetylation and sulfation of a glycosaminoglycan; antibodies to the polypeptides of the invention; and therapeutic uses of these compounds are disclosed.

17 Claims, 16 Drawing Sheets

Primer 1s    5' GCI AA$^C_T$ TA$^C_T$ TT$^C_T$ GA$^C_T$ $^{TC}_{AG}$I GA$^G_A$ GT         3'

Peptide 1   Ser Ala Asn Tyr Phe Asp Ser Glu Val Ala Pro Arg

Peptide 2          Asp His Asn Ile Glu Leu Ser Lys
Primer 2a    3' CT$^G_A$ GT$^G_A$ TT$^G_A$ TAI CT$^C_T$ $^G_A$AI $^{TC}_{AG}$I TT$^C_T$         5'

Primer 3s    5' GCI CA$^C_T$ GA$^C_T$ GA$^C_T$ CCI GTI GT$^{A}_{C/T/G}$ $^C_T$T         3'

Peptide 3   Ala His Asp Asp Pro Val Ala Leu Lys

Primer 3a    3'  GT$^G_A$ CT$^G_A$ CT$^G_A$ GGI CAI CGI $^G_A$AI TT$^C_T$         5'

FIG. 1A

```
GAATTCCAAG ACAGAATATC AGTCCTCCCT CCGTTTCCCA GGTCAGCTCC CTAGCCTTTA    60

CCCTGTGGGC CCAACGTGAA GAGCGTGAAG AGCGCGGCAT GCAGCACCCC CTGGCTGGCC   120

CGGTGTCTTT TGACCTGCTG TTGACTGCTC CCAGGAGGCC CTGACGCCCT GGGGCACTTT   180

TGCTCTGCAC AGGACCACGT TGGGGTTTGC CATGGTGACA TAAAGGGGTG TAGAGGAAGG   240

AAGGAGCAAG ACCAGCCTGT AGACTGTGCC CCTGGCTGGG CGAAAGGGCC AGGGGCCCGG   300

AGCCTTCTCT CCACTGCCCT CTGAACGTCT CACTTCCTAA GTCTCTGCAT TTCTCAGTCA   360

GTGGACAACT TTTGGAACTC CTGTGTGAGG ACTTCGGGGG ACCAGGCCAG GCTGGGCCTC   420

TGCTGGTTGA GATCTCGGGG GCCAGA                                        446
```

```
ATG CCT GCC CTG GCG TGC CTC CGG AGG CTG TGT CGG CAC CTG TCC CCA    494
Met Pro Ala Leu Ala Cys Leu Arg Arg Leu Cys Arg His Leu Ser Pro
1             5                  10                 15

CAG GCT GTC CTG TTC CTG CTG TTT GTC TTC TGC CTG TTC AGC GTG TTT    542
Gln Ala Val Leu Phe Leu Leu Phe Val Phe Cys Leu Phe Ser Val Phe
          20                  25                 30

GTC TCG GCC TAC TAC CTA TAT GGT TGG AAC CGG GGC CTC GAG CCC TCG    590
Val Ser Ala Tyr Tyr Leu Tyr Gly Trp Asn Arg Gly Leu Glu Pro Ser
          35                40                    45

GCA GAT GCT TCT GAG TCC GAC TGC GGG GAC CCA CCA CCT GTC GCC CCT    638
Ala Asp Ala Ser Glu Ser Asp Cys Gly Asp Pro Pro Pro Val Ala Pro
50                  55                 60

AGC CGT CTC CTG CCA ATC AAG CCT GTG CAG GCG GTC GCC CCT TCT CGA    686
Ser Arg Leu Leu Pro Ile Lys Pro Val Gln Ala Val Ala Pro Ser Arg
65                  70                 75                    80

ACA GAC CCG CTG GTG CTG GTA TTT GTG GAG AGC CTC TAT TCA CAG CTG    734
Thr Asp Pro Leu Val Leu Val Phe Val Glu Ser Leu Tyr Ser Gln Leu
                85                 90                    95

GGC CAG GAG GTG GTG GCC ATC CTG GAA TCC AGT CGC TTC AAG TAC CGA    782
Gly Gln Glu Val Val Ala Ile Leu Glu Ser Ser Arg Phe Lys Tyr Arg
              100                 105                110

ACA GAA ATT GCA CCG GGG AAG GGG GAC ATG CCC ACA CTC ACA GAC AAG    830
Thr Glu Ile Ala Pro Gly Lys Gly Asp Met Pro Thr Leu Thr Asp Lys
          115                 120                125

GGC CGA GGC CGC TTC GCC CTC ATC ATC TAT GAG AAC ATC CTC AAG TAT    878
Gly Arg Gly Arg Phe Ala Leu Ile Ile Tyr Glu Asn Ile Leu Lys Tyr
130                 135                    140
```

FIG. 3A

```
GTC AAC CTG GAT GCC TGG AAC CGG GAG CTG CTG GAC AAG TAC TGT GTG        926
Val Asn Leu Asp Ala Trp Asn Arg Glu Leu Leu Asp Lys Tyr Cys Val
145                 150                 155                 160

GCC TAC GGC GTG GGC ATC ATT GGC TTC TTC AAG GCC AAT GAG AAC AGC        974
Ala Tyr Gly Val Gly Ile Ile Gly Phe Phe Lys Ala Asn Glu Asn Ser
                165                 170                 175

CTG CTG AGT GCA CAG CTC AAA GGC TTC CCT CTT TTC CTG CAT TCG AAC       1022
Leu Leu Ser Ala Gln Leu Lys Gly Phe Pro Leu Phe Leu His Ser Asn
            180                 185                 190

CTG GGC TTG AAA GAC TGC AGC ATC AAC CCC AAG TCC CCA CTG CTG TAC       1070
Leu Gly Leu Lys Asp Cys Ser Ile Asn Pro Lys Ser Pro Leu Leu Tyr
                195                 200                 205

GTG ACA CGG CCC AGT GAG GTA GAG AAA GGT GTG CTG CCC GGA GAG GAC       1118
Val Thr Arg Pro Ser Glu Val Glu Lys Gly Val Leu Pro Gly Glu Asp
        210                 215                 220

TGG ACG GTG TTC CAG TCT AAC CAC TCT ACC TAT GAG CCA GTG CTG CTG       1166
Trp Thr Val Phe Gln Ser Asn His Ser Thr Tyr Glu Pro Val Leu Leu
                        ●
225                 230                 235                 240

GCC AAG ACG CGC TCC TCT GAG TCC ATC CCA CAC CTG GGC GCA GAT GCC       1214
Ala Lys Thr Arg Ser Ser Glu Ser Ile Pro His Leu Gly Ala Asp Ala
                245                 250                 255

GGC CTG CAT GCT GCC CTG CAC GCT ACT GTG GTC CAG GAC CTG GGC CTC       1262
Gly Leu His Ala Ala Leu His Ala Thr Val Val Gln Asp Leu Gly Leu
            260                 265                 270

CAT GAC GGC ATT CAG CGT GTG CTG TTT GGC AAC AAC CTC AAC TTT TGG       1310
His Asp Gly Ile Gln Arg Val Leu Phe Gly Asn Asn Leu Asn Phe Trp
        275                 280                 285

CTG CAT AAG CTC GTC TTC GTG GAC GCT GTG GCC TTC CTC ACA GGG AAG       1358
Leu His Lys Leu Val Phe Val Asp Ala Val Ala Phe Leu Thr Gly Lys
        290                 295                 300

CGC CTC TCA CTG CCT TTG GAC CGA TAC ATC CTG GTG GAC ATT GAT GAC       1406
Arg Leu Ser Leu Pro Leu Asp Arg Tyr Ile Leu Val Asp Ile Asp Asp
305                 310                 315                 320

ATT TTT GTA GGC AAG GAG GGC ACA CGC ATG AAG GTG GAG GAT GTG AAG       1454
Ile Phe Val Gly Lys Glu Gly Thr Arg Met Lys Val Glu Asp Val Lys
                325                 330                 335
```

FIG. 3B

| | | | | | | | | | | | | | | | | |
|---|---|---|---|---|---|---|---|---|---|---|---|---|---|---|---|---|
| GCC | CTG | TTT | GAT | ACA | CAG | AAT | GAA | CTT | CGT | ACA | CAT | ATC | CCA | AAC | TTC | 1502 |
| Ala | Leu | Phe | Asp | Thr | Gln | Asn | Glu | Leu | Arg | Thr | His | Ile | Pro | Asn | Phe | |
| | | | 340 | | | | | 345 | | | | | 350 | | | |
| ACC | TTC | AAC | CTG | GGC | TAC | TCA | GGG | AAA | TTC | TTC | CAC | ACA | GGT | ACC | GAT | 1550 |
| Thr | Phe | Asn | Leu | Gly | Tyr | Ser | Gly | Lys | Phe | Phe | His | Thr | Gly | Thr | Asp | |
| | | 355 | | | | | 360 | | | | | 365 | | | | |
| GCT | GAG | GAT | GCT | GGG | GAC | GAC | CTG | CTG | CTG | TCC | TAT | GTG | AAA | GAG | TTC | 1598 |
| Ala | Glu | Asp | Ala | Gly | Asp | Asp | Leu | Leu | Leu | Ser | Tyr | Val | Lys | Glu | Phe | |
| | | 370 | | | | | 375 | | | | | 380 | | | | |
| TGG | TGG | TTC | CCC | CAC | ATG | TGG | AGC | CAT | ATG | CAA | CCC | CAC | CTC | TTC | CAC | 1646 |
| Trp | Trp | Phe | Pro | His | Met | Trp | Ser | His | Met | Gln | Pro | His | Leu | Phe | His | |
| 385 | | | | | 390 | | | | 395 | | | | | 400 | | |
| AAC | CAG | TCT | GTG | CTG | GCT | GAG | CAG | ATG | GCC | CTG | AAC | AAG | AAG | TTC | GCT | 1694 |
| Asn | Gln | Ser | Val | Leu | Ala | Glu | Gln | Met | Ala | Leu | Asn | Lys | Lys | Phe | Ala | |
| ● | | | | 405 | | | | | 410 | | | | | 415 | | |
| GTC | GAG | CAC | CCC | ATT | GGG | ACA | GAT | ATG | GGG | TAT | GCA | GTG | GCA | CCC | CAC | 1742 |
| Val | Glu | His | Pro | Ile | Gly | Thr | Asp | Met | Gly | Tyr | Ala | Val | Ala | Pro | His | |
| | | | 420 | | | | | 425 | | | | | 430 | | | |
| CAC | TCT | GGT | GTG | TAC | CCT | GTG | CAT | GTG | CAG | CTG | TAT | GAG | GCC | TGG | AAG | 1790 |
| His | Ser | Gly | Val | Tyr | Pro | Val | His | Val | Gln | Leu | Tyr | Glu | Ala | Trp | Lys | |
| | | 435 | | | | | 440 | | | | | 445 | | | | |
| CAA | GTG | TGG | AAC | ATC | CGT | GTG | ACC | AGC | ACA | GAG | GAG | TAC | CCG | CAT | CTG | 1838 |
| Gln | Val | Trp | Asn | Ile | Arg | Val | Thr | Ser | Thr | Glu | Glu | Tyr | Pro | His | Leu | |
| | 450 | | | | | 455 | | | | | 460 | | | | | |
| AAG | CCT | GCC | CGT | TAC | CGC | CGT | GGC | TTC | ATC | CAC | AAT | GGC | ATC | ATG | GTC | 1886 |
| Lys | Pro | Ala | Arg | Tyr | Arg | Arg | Gly | Phe | Ile | His | Asn | Gly | Ile | Met | Val | |
| 465 | | | | 470 | | | | | 475 | | | | | 480 | | |
| CTC | CCT | CGG | CAG | ACC | TGT | GGT | CTC | TTT | ACA | CAC | ACC | ATC | TTC | TAC | AAC | 1934 |
| Leu | Pro | Arg | Gln | Thr | Cys | Gly | Leu | Phe | Thr | His | Thr | Ile | Phe | Tyr | Asn | |
| | | | | 485 | | | | | 490 | | | | | 495 | | |
| GAG | TAC | CCT | GGA | GGC | TCC | AGT | GAG | CTG | GAC | AAG | ATC | ATC | AAT | GGG | GGC | 1982 |
| Glu | Tyr | Pro | Gly | Gly | Ser | Ser | Glu | Leu | Asp | Lys | Ile | Ile | Asn | Gly | Gly | |
| | | | 500 | | | | | 505 | | | | | 510 | | | |
| GAG | CTC | TTT | CTT | ACT | GTG | CTC | CTC | AAT | CCT | ATC | AGC | GTC | TTC | ATG | ACA | 2030 |
| Glu | Leu | Phe | Leu | Thr | Val | Leu | Leu | Asn | Pro | Ile | Ser | Val | Phe | Met | Thr | |
| | | 515 | | | | | 520 | | | | | 525 | | | | |
| CAC | TTA | TCC | AAC | TAT | GGA | AAT | GAC | CGC | CTG | GGA | CTG | TAC | ACC | TTC | AAG | 2078 |
| His | Leu | Ser | Asn | Tyr | Gly | Asn | Asp | Arg | Leu | Gly | Leu | Tyr | Thr | Phe | Lys | |
| | | 530 | | | | | 535 | | | | | 540 | | | | |

FIG. 3C

```
CAC CTG GTG CGC TTC CTG CAC TCC TGG ACC AAC CTG AGG CTG CAG ACG    2126
His Leu Val Arg Phe Leu His Ser Trp Thr Asn Leu Arg Leu Gln Thr
545             550                 555                 560

CTG CCC CCT GTG CAG CTG GCC CAG AAG TAC TTC CAG ATC TTT TCT GAG    2174
Leu Pro Pro Val Gln Leu Ala Gln Lys Tyr Phe Gln Ile Phe Ser Glu
                565                 570                 575

GAG AAG GAC CCA CTT TGG CAG GAT CCC TGT GAG GAC AAA CGC CAC AAA    2222
Glu Lys Asp Pro Leu Trp Gln Asp Pro Cys Glu Asp Lys Arg His Lys
            580                 585                 590

GAC ATC TGG TCT AAG GAG AAG ACA TGT GAT CGC TTC CCA AAG CTG CTC    2270
Asp Ile Trp Ser Lys Glu Lys Thr Cys Asp Arg Phe Pro Lys Leu Leu
        595                 600                 605

ATC ATT GGC CCC CAG AAA ACA GGC ACC ACA GCC CTC TAC CTG TTC CTG    2318
Ile Ile Gly Pro Gln Lys Thr Gly Thr Thr Ala Leu Tyr Leu Phe Leu
    610                 615                 620

GGC ATG CAC CCC GAC CTC AGC AGC AAC TAC CCC AGC TCC GAG ACC TTT    2366
Gly Met His Pro Asp Leu Ser Ser Asn Tyr Pro Ser Ser Glu Thr Phe
625                 630                 635                 640

GAG GAG ATC CAG TTT TTT AAT GGC CAC AAC TAT CAC AAA GGC ATC GAC    2414
Glu Glu Ile Gln Phe Phe Asn Gly His Asn Tyr His Lys Gly Ile Asp
                645                 650                 655

TGG TAC ATG GAA TTC TTC CCT ATT CCC TCC AAC ACC ACC TCT GAC TTC    2462
Trp Tyr Met Glu Phe Phe Pro Ile Pro Ser Asn Thr Thr Ser Asp Phe
            660                 665   ●           670

TAC TTT GAA AAA AGT GCC AAC TAC TTT GAT TCA GAA GTG GCA CCA CGG    2510
Tyr Phe Glu Lys Ser Ala Asn Tyr Phe Asp Ser Glu Val Ala Pro Arg
        675                 680                 685

CGA GCA GCT GCC CTA TTG CCC AAG GCC AAG GTT CTC ACC ATC CTC ATC    2558
Arg Ala Ala Ala Leu Leu Pro Lys Ala Lys Val Leu Thr Ile Leu Ile
    690                 695                 700

AAT CCA GCC GAC CGG GCT TAC TCC TGG TAC CAG CAC CAG CGG GCC CAT    2606
Asn Pro Ala Asp Arg Ala Tyr Ser Trp Tyr Gln His Gln Arg Ala His
705                 710                 715                 720

GAT GAC CCG GTG GCC CTA AAG TAC ACC TTC CAT GAG GTG ATC ACA GCT    2654
Asp Asp Pro Val Ala Leu Lys Tyr Thr Phe His Glu Val Ile Thr Ala
                725                 730                 735

GGC CCT GAC GCA TCC TCA AAG CTG CGT GCC CTC CAG AAC CGA TGC CTG    2702
Gly Pro Asp Ala Ser Ser Lys Leu Arg Ala Leu Gln Asn Arg Cys Leu
            740                 745                 750

GTC CCC GGC TGG TAT GCC ACT CAT ATT GAA CGC TGG CTC AGC GCC TTT    2750
Val Pro Gly Trp Tyr Ala Thr His Ile Glu Arg Trp Leu Ser Ala Phe
        755                 760                 765
```

FIG. 3D

```
CAT GCC AAC CAG ATC CTG GTC TTG GAT GGC AAA CTG CTG CGA ACA GAA    2798
His Ala Asn Gln Ile Leu Val Leu Asp Gly Lys Leu Leu Arg Thr Glu
    770                 775                 780

CCT GCC AAA GTG ATG GAC ACA GTG CAG AAA TTC CTC GGG GTG ACC AGC    2846
Pro Ala Lys Val Met Asp Thr Val Gln Lys Phe Leu Gly Val Thr Ser
785                 790                 795                 800

ACG GTT GAC TAC CAT AAA ACC TTG GCG TTT GAC CCA AAG AAA GGA TTT    2894
Thr Val Asp Tyr His Lys Thr Leu Ala Phe Asp Pro Lys Lys Gly Phe
                805                 810                 815

TGG TGC CAG CTG CTC GAA GGA GGA AAA ACC AAG TGT CTG GGA AAA AGC    2942
Trp Cys Gln Leu Leu Glu Gly Gly Lys Thr Lys Cys Leu Gly Lys Ser
            820                 825                 830

AAG GGA CGG AAA TAT CCA GAG ATG GAC CTG GAT TCC CGA GCC TTC CTA    2990
Lys Gly Arg Lys Tyr Pro Glu Met Asp Leu Asp Ser Arg Ala Phe Leu
        835                 840                 845

AAG GAT TAC TAC CGG GAC CAC AAC ATT GAG CTC TCT AAG CTG CTG TAT    3038
Lys Asp Tyr Tyr Arg Asp His Asn Ile Glu Leu Ser Lys Leu Leu Tyr
    850             ═══855═══════════════860═══

AAG ATG GGC CAG ACA CTG CCC ACC TGG CTG CGG GAA GAC CTC CAG AAC    3086
Lys Met Gly Gln Thr Leu Pro Thr Trp Leu Arg Glu Asp Leu Gln Asn
865 ═══════════════870═══                 875                 880

ACC AGG                                                             3092
Thr Arg
```

FIG. 3E

```
TAGCCTTGGC CACCACAGCC AGCCAGAACG CTTGTGTTAG CAGGGATGTC CTGCCTCACA 3152

CTGAGCCAGA CTGACCTGCC TCGAAGGATG CTGGCCCCAG CCAGCCAGGA GCAACGAGCA 3212

ATACCCTGCT AAGGCCCACC AGAGCCGGAA GCCCAGGCAG GTCTGCCCTC TGTGGGACCA 3272

GAGGTCCATT CCGTTCCTTC GCAGCCTCCC TGCCTGGGGA GAGCACAAGC GCCTCAGAGC 3332

ATCCACTGCT GGATGTGTGG CTGTGGGATT CCTGTTGGTG GAAGGTCATT TCCTGGTAGG 3392

AGGAGTCCTG GAGACTCTCT CCTGTCCCTC ACTGTGTTCG GCCAGTCCTG CCCTGTTCTG 3452

TGTCATACCA CCCCTGCTCC AGCAGGATGT CCCCTCAGTA TTAGCTGTCA TATTTCTCTG 3512

TCCTCCAGAC AGTAAGGGAG AGGAGCGCAG CTGGGCCTCT CGCCCAACTA GAGAGAAAGA 3572

CTGGGCATGT CCCTGAGGGT TTGAGCCAGG CCCCGCCAGG GTTTAGGTAG GCACCCAGAT 3632

GCACTCATAG ATTGAATGTG AGGGTGGCCA TCTTGAGAGG ACATACGACT CAGTATTTGG 3692

GTTATTAGTA TCAATCTCAT CTCCCCTTTG GGGAAAGAC TCTCTGGTCC CCTATTGTAT 3752

CCACCTAGTG CTCATGGTCT CTTGTTGGCC CTGGGCCACT GCCCTGCCAC TGGGCCCAGA 3812

GACATGGGCC TTGGCCCTGT CCTGTTCACC TGGATGTGAC CTGTGGTGTT TCCTGTGGTA 3872

AAGGCTGAGG CGAGTCAGGA GTCTGCCAGT GTTCATACTC CCATGTACAT ATACACTGTC 3932

TCCCAGCCAC CGCCTCGGCC CGGCAGGCAA GCAGAGTCAG CAGCACTGCT CTCTACTGCT 3992

TTGCCTGGCA ACCTGTGGCT GAGGGTCCCC AGAGACCCCC CCAACCTCCC AAATACTAAG 4052
```

GLYCOSAMINOGLYCAN SPECIFIC SULFOTRANSFERASES

Partial funding of the work described herein was provided under #GM 34396 awarded by the National Institutes of Health, and the U.S. government has certain rights to the invention.

BACKGROUND OF THE INVENTION

This application is a continuation-in-part of U.S. Ser. No. 07/899,423 filed Jun. 16, 1992, now abandoned.

The present invention relates generally to sulfotransferases and more specifically to sulfotransferases which also have deacetylase activity.

Sulfotransferases are enzymes which are involved in the transfer of sulfate from adenosine 3'phosphate phosphosulfate (PAPS) to specific substrates such as growing proteoglycans (Horwitz et al., *J. Cell Biol.* 38:358, 1968; Young et al., *J. Cell Biol.* 57:175,1973), tyrosines of proteins (Lee et al., *Proc. Nat. Acad. Sci.* USA 82:6143, 1985), and sugars of glycoproteins and glycolipids (Green et al., *Proc. Natl. Acad. Sci.* USA 81:5320, 1984; Fleischer et al. *J. Biol. Chem.* 249; 5995, 1974).

In one particular example of a sulfotransferase-mediated reaction, the biosynthesis of sulfated proteoglycans such as the glycosaminoglycans, heparin and heparan sulfate, occurs in a precise, stepwise manner. Once the polysaccharide polymers have been formed they undergo a series of modification reactions. These include, in sequence, N-deacetylation and N-sulfation of glucosamine, C- 5 epimerization of D-glucuronic acid to L-iduronic acid, and 2-O-sulfation at various positions (Lindahl et al., *Trends Biochem. Sci.* 11:221–225, 1986; Lindahl et al. in *Biology of Protoglycans*, Wight et al. eds., pp. 59, Academic Press, New York, 1987; Lindahl in *Heparin: Chemical and Biological Properties, Clinical Applications*, Lane et al., eds., pp.159, Edward Arnold, London, 1989). The quantity and distribution of each biosynthetic enzyme appears to determine not only the extent of the respective modification but also the extent of subsequent modifications. For example, the N-deacetylation of N-acetyl-D-glucosamine residues is required for the N-sulfation reaction to occur and these two reactions appear to be tightly coupled; free glucosamine residues are rarely found in heparan sulfate or heparin. This is true even in the case of a Chinese hamster ovary (CHO) cell mutant where the N-sulfotransferase is significantly reduced in activity (Bame et al., *J. Biol. Chem.* 266:12461–12468, 1991). In addition, both C-5-epimerization and O-sulfation appear to occur exclusively in the vicinity of previously incorporated N-sulfate groups.

Currently, most preparations of sulfated proteoglycans, e.g., heparin and heparan sulfate, are composed of a structurally complex mixture of molecules with varying levels of modification and biological activity; in particular, molecules with higher levels of modification generally demonstrate higher levels of biological activity. This is due to the fact that the polymer-modification reactions are generally incomplete, such that a fraction of the potential targets escape modification at each step. Thus, methods for improving the efficiency of proteoglycan modification should enable the production of preparations of proteoglycans which demonstrate high levels of biological activity. An important step toward the production of such highly active sulfated proteoglycans is the isolation of the sulfotransferases (including the genes and recombinant proteins) involved in the sulfation cascade.

SUMMARY OF THE INVENTION

In general, the invention features isolated DNA comprising a DNA sequence encoding a polypeptide of an animal which is capable of catalyzing the deacetylation and sulfation of a glycosaminoglycan, i.e., is a glycosaminoglycan specific deacetylase/sulfotransferase. Preferably the animal is a mammal such as a rat or a human. Also preferably, the isolated DNA encodes a polypeptide which is capable of specifically catalyzing the N-deacetylation and N-sulfation of a glycosaminoglycan. Even more preferably, the DNA encodes an enzyme which is capable of catalyzing the N-deacetylation and N-sulfation of heparin and/or heparan sulfate, and most preferably the DNA encodes a N-heparan sulfate-N-deacetylase/N-sulfotransferase and is homologous to all or part of the DNA sequence shown in FIG. 3 (SEQ ID NO:1).

By "isolated" is meant a DNA that is not immediately contiguous with (i.e., covalently linked to) both of the coding sequences with which it is immediately contiguous in the naturally occurring genome of the organism from which the DNA of the invention is derived. The term therefore includes, for example, a recombinant DNA which is incorporated into a vector (e.g., an autonomously replicating virus or plasmid), or into the genomic DNA of a prokaryote or eukaryote; DNA which exists as a separate molecule independent of other DNA sequences such as a cDNA or genomic DNA fragment produced by chemical means (e.g., polymerase chain reaction), or by restriction endonuclease treatment; and recombinant DNA which is part of a hybrid gene encoding additional polypeptide sequence(s). Also included in the isolated DNAs of the invention are single-stranded DNAs which are generally at least 18 nucleotides long, preferably at least 30 nucleotides long, ranging up to full length of the gene or cDNA. The single-stranded DNAs may also be detectably labelled for use as hybridization probes, and may be antisense.

"Homologous", as used herein in reference to DNA molecules, refers to the subunit sequence similarity between two DNA molecules. When a subunit position in both of the DNA molecules is occupied by the same monomeric subunit, i.e., nucleotide, then they are homologous at that position. The homology between two sequences is a direct function of the number of matching or homologous positions, e.g., if half of the positions in two DNA sequences are homologous then they are 50% homologous. By "substantially homologous" is meant largely but not wholly homologous.

In one related aspect, the invention features isolated DNA comprising a DNA sequence encoding a polypeptide capable of catalyzing the sulfation of a glycosaminoglycan, preferably the N-sulfation of a glycosaminoglycan, e.g., heparin or heparan sulfate.

In another related aspect, the invention also features isolated DNA comprising a DNA sequence encoding a polypeptide capable of catalyzing the deacetylation of a glycosaminoglycan, preferably the N-deacetylation of a glycosaminoglycan, e.g., heparin or heparan sulfate.

In other related aspects, the invention features a vector or a recombinant cell containing an isolated DNA sequence encoding a polypeptide capable of catalyzing the sulfation, deacetylation or both the deacetylation and sulfation of a glycosaminoglycan. The vector may be provided as a purified preparation (e.g., a vector separated from the mixture of vectors which make up a library). The cell may be a prokaryotic or eukaryotic cell (e.g., a yeast or mammalian cell), and is preferably an essentially homogenous population of cells which contain the isolated DNA of the invention. By "essentially homogenous" is meant that at least 90% of the cells contain the isolated DNA of the invention (e.g., incorporated into the genome of the cell, or contained within an episomal self-replicating vector). Preferably, the vector is capable of directing expression of a polypeptide which catalyzes the sulfation and deacetylation of a glycosaminoglycan, e.g., heparin or heparan sulfate, a polypeptide which catalyzes the sulfation of the glycosaminoglycan, or a polypeptide which catalyzes the deacetylation of the glycosaminoglycan. Most preferably, the vector is capable of directing the expression of a N-heparan sulfate-N-deacetylase-N-sulfotransferase.

In addition, the nucleic acids of the invention can be used as probes to enable one of ordinary skill in the art of genetic engineering to identify and clone glycosaminoglycan specific sulfotransferase and/or deacetylase/sulfotransferase homologs from any species, expanding the usefulness of the sequences of the invention.

In a further aspect, the invention features a polypeptide capable of catalyzing the deacetylation and sulfation of a glycosaminoglycan produced by expression of a recombinant DNA molecule. Preferably, the polypeptide is capable of catalyzing the sulfation of heparin and/or heparan sulfate, more preferably is capable of specifically catalyzing the N-deacetylation and N-sulfation of heparin and/or heparan sulfate, and most preferably is an N-heparan sulfate-N-deacetylase/N-sulfotransferase. Included in this aspect of the invention is a substantially pure preparation of a recombinantly produced glycosaminoglycan specific deacetylase/sulfotransferase. As used herein, the term "substantially pure" describes a preparation which is at least 60% by weight the compound of interest, e.g., a protein or a polypeptide, e.g., a glycosaminoglycan specific deacetylase/sulfotransferase or a fragment thereof. Preferably the preparation is at least 75%, more preferably at least 90%, and most preferably at least 99%, by weight the compound of interest. Purity can be measured by any appropriate method, e.g., in the case of polypeptides by column chromatography, polyacrylamide gel electrophoresis, or HPLC analysis. Also included in this aspect of the invention are polypeptides capable of inducing either the deacetylation, sulfation, or both the deacetylation and sulfation of various molecules, preferably glycosaminoglycans. These polypeptides may be produced by expression of all or part of the isolated DNA of the invention. Specific polypeptide fragments of particular interest include, but are not limited to, soluble polypeptides in which the membrane-binding domain, (as deduced from the primary amino acid sequence), has been removed and polypeptide fragments which display altered substrate specificity from that of the intact enzyme. Techniques for generating and testing such polypeptides are well known to those skilled in the art. The polypeptides of this aspect of the invention may be purified and are especially useful in methods for the manufacture of deacetylated and/or sulfated molecules including glycosaminoglycans, proteoglycans, glycolipids, polysaccharides, and tyrosine residues on proteins from both eukaryotic and prokaryotic species.

In yet another aspect, the invention features an antibody, and a purified preparation of an antibody, which is capable of specifically binding to a glycosaminoglycan specific deacetylase/sulfotransferase. By "specifically binding" is meant an antibody which binds to a glycosaminoglycan specific deacetylase/sulfotransferase or a fragment thereof, and which does not substantially recognize and bind to other antigenically-unrelated molecules.

Antibodies according to the invention may be prepared by a variety of methods well known to those skilled in the art. For example, cells expressing a glycosaminoglycan deacetylase/sulfotransferase or antigenic fragments thereof can be administered to an animal in order to induce the production of polyclonal antibodies. Alternatively, antibodies according to the invention may be monoclonal antibodies. Such monoclonal antibodies can be prepared using hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., *In Monoclonal Antibodies and T Cell Hybridomas*, Elsevier, N.Y., 1981). Antibodies of the invention include those which are capable of neutralizing (i.e., partially or completely inhibiting) one or both catalytic activities of the enzyme, as well as those which are capable of forming an immune complex with the deacetylase/sulfotransferase without interfering with sulfation or deacetylation of glycosaminoglycan molecules.

Because deacetylase/sulfotransferase substrates appear to be involved in a number of important physiological functions, the deacetylase/sulfotransferase peptides, nucleic acids, and antibodies of the invention provide useful therapeutics for a number of disorders. They also provide the means for obtaining other useful therapeutics, for example, highly modified and therefore highly active sulfated proteoglycans. For example, proteoglycans containing heparin and/or heparan sulfate are present in a variety of basement membranes (Kanwar et al., *Proc. Natl. Acad. Sci. USA* 81:762, 1984), extracellular matrices (Heinegard et al., in *Biochemistry of the Extracellular Matrix*, pp. 277–328, Elsevier Scientific Publishing Co., Inc., N.Y., 1984), and cell membranes (Kjellen et al., *Proc. Natl. Acad. Sci. USA* 78:537, 1981), and have been implicated in several important biological functions, such as blood clotting (Lindahl et al., *J. Biol. Chem.* 259:12368, 1984), cell recognition (Lupa et al., *Dev. Biol.* 142:31, 1990), and cell adhesion (LeBaron et al., *J. Cell Biol.* 106:945, 1988; LeBaron et al., *J. Biol. Chem.* 264:7950, 1989).

Heparin and heparan sulfate are also believed to be involved in normal and tumor cell growth. Heparan sulfate proteoglycans (HSPGs) found on the cell surface and in the extracellular matrix have been found to be low affinity receptors for basic fibroblast growth factor (bFGF) and are required for the binding of bFGF to its high-affinity receptor (Yayon et al., *Cell* 64:841, 1991; Klagsbrun et al., *Cell* 67:229, 1991). Moreover, reduction of the sulfation of heparan sulfate substantially reduces binding of bFGF to its cell surface receptors (Rapraeger et al., *Science* 252:1705, 1991) and, in cells which are deficient in heparan sulfate, the addition of free heparin and heparan sulfate can reconstitute a low affinity receptor. Thus, the mitogenic effects of bFGF on cells of mesenchymal and neuroectodermal origin are dependent on the presence of heparan sulfate and/or heparin.

Accordingly, the invention also features therapeutic compositions including, in a pharmaceutically acceptable carrier, (a) a glycosaminoglycan specific deacetylase/sulfotransferase, (b) a polypeptide containing a fragment of a glycosaminoglycan specific deacetylase/sulfotransferase; the peptide having either sulfotransferase activity, deacetylase activity or both sulfotransferase and deacetylase activity, (c) an antibody which specifically binds to a glycosaminoglycan specific deacetylase/sulfotransferase, (d) a single-stranded DNA molecule which encodes a glycosaminoglycan specific deacetylase/sulfotransferase, or (e) a single-stranded DNA molecule which is antisense to DNA which encodes a glycosaminoglycan specific deacetylase/sulfotransferase. These therapeutic compositions can be administered to an animal, preferably a human, as a means for treating various conditions wherein the stimulation or inhibition of either the deacetylation, sulfation, or both deacetylation and sulfation of glycosaminoglycans is desirable.

Other features and advantages of the invention will be apparent from the following description and from the claims.

DETAILED DESCRIPTION

The drawings will first be briefly described.

Drawings FIG. 1 shows (A) a representation of the oligonucleotide primer sequences 1s (SEQ ID NO:2), 2a (SEQ ID NO:3), 3s (SEQ ID NO:4), and 3a (SEQ ID NO:5) derived from rat liver N-heparan sulfate sulfotransferase tryptic peptides 1 (SEQ ID NO:6), 2 (SEQ ID NO:7), and 3 (SEQ ID NO:8); (B) a representation of an agarose gel of the PCR products obtained using the primers depicted in (A); and (C) a schematic depiction of the proposed alignment of rat liver N-heparan sulfate sulfotransferase tryptic peptides 1 (SEQ ID NO:6), 2 (SEQ ID NO:7), and 3 (SEQ ID NO:8) based on the results of PCR and sequencing analyses.

FIGS. 3A to 3F are is a representation of the nucleic acid and predicted amino acid sequence of the rat N-heparan sulfate sulfotransferase cDNA (SEQ ID NO:1).

Figure 5:
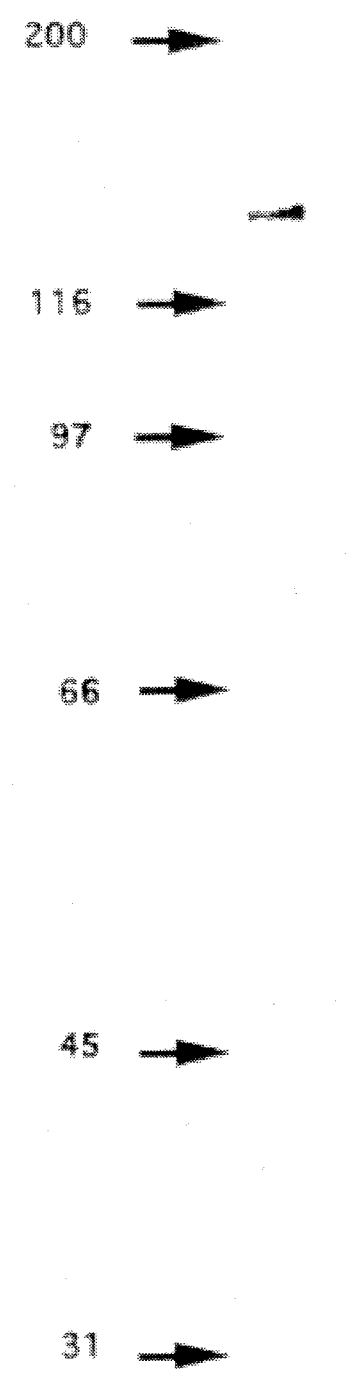

FIG. 5 is a photograph of a gradient SDS-PAGE (8%–20%) gel of one hundred ng of soluble enzyme that had been purified and eluted by rabbit IgG-agarose affinity chromatography. The gel was stained with silver nitrate. The molecular weights of marker proteins are indicated (in Kda).

Figure 6A:
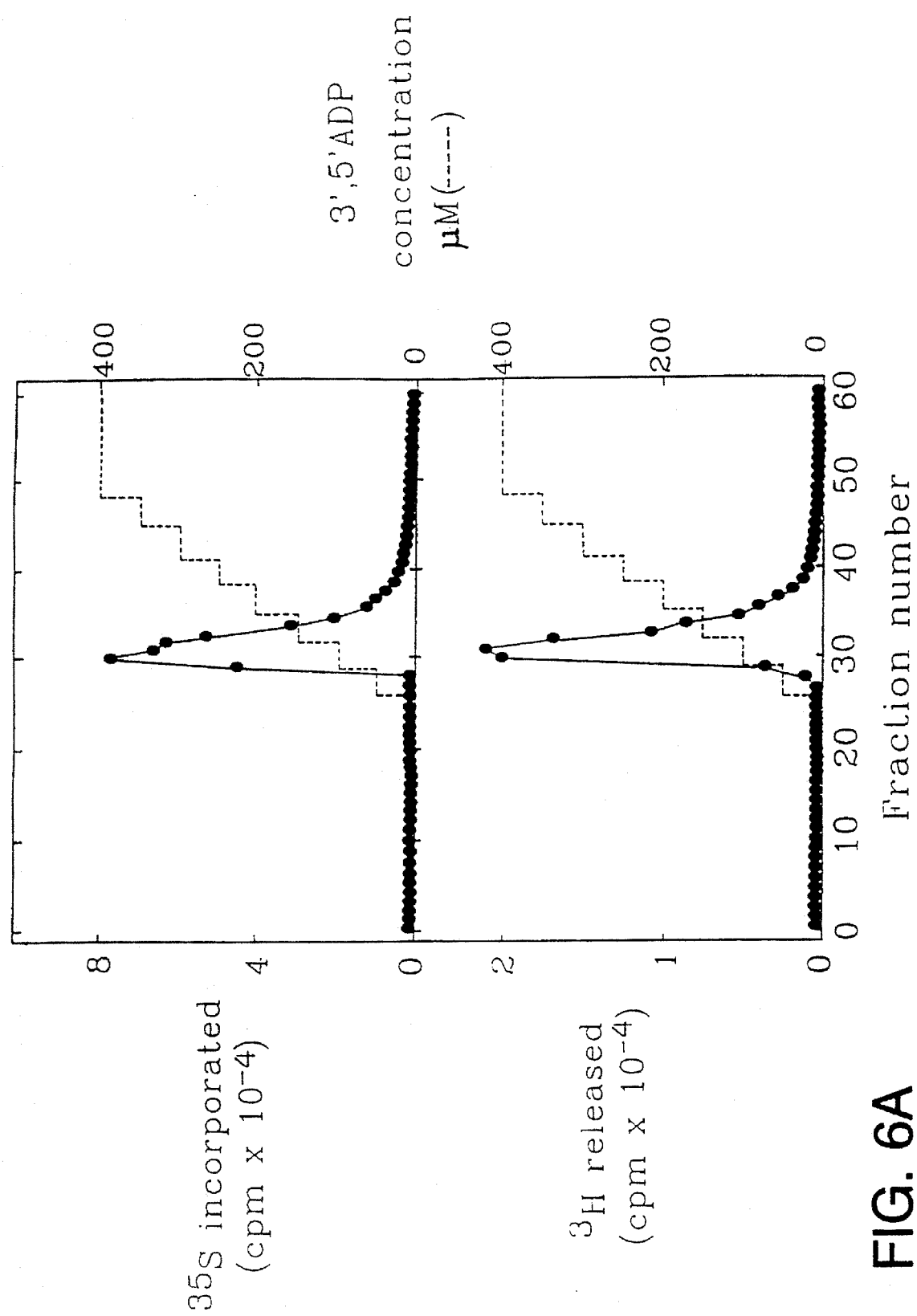

FIG. 6A is a graph which depicts the coelution of N-sulfotransferase (top) and N-deacetylase (bottom) activities of the soluble form of N-HSST on 3',5'-ADP-agarose column.

Figure 6B:
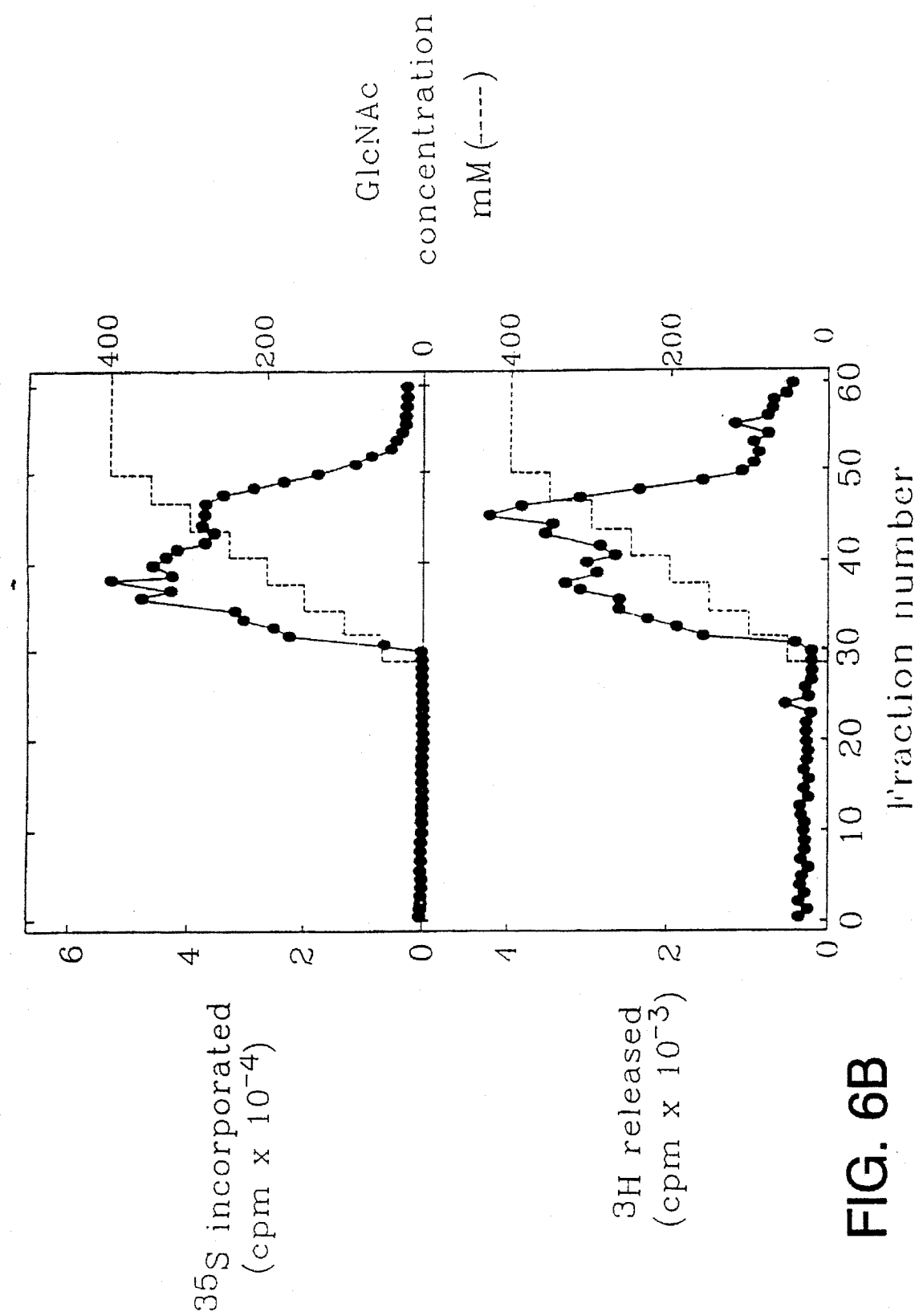

FIG. 6B is a graph which depicts the coelution of N-sulfotransferase (top) and N-deacetylase (bottom) activities on a WGA sepharose column.

Figure 7A:
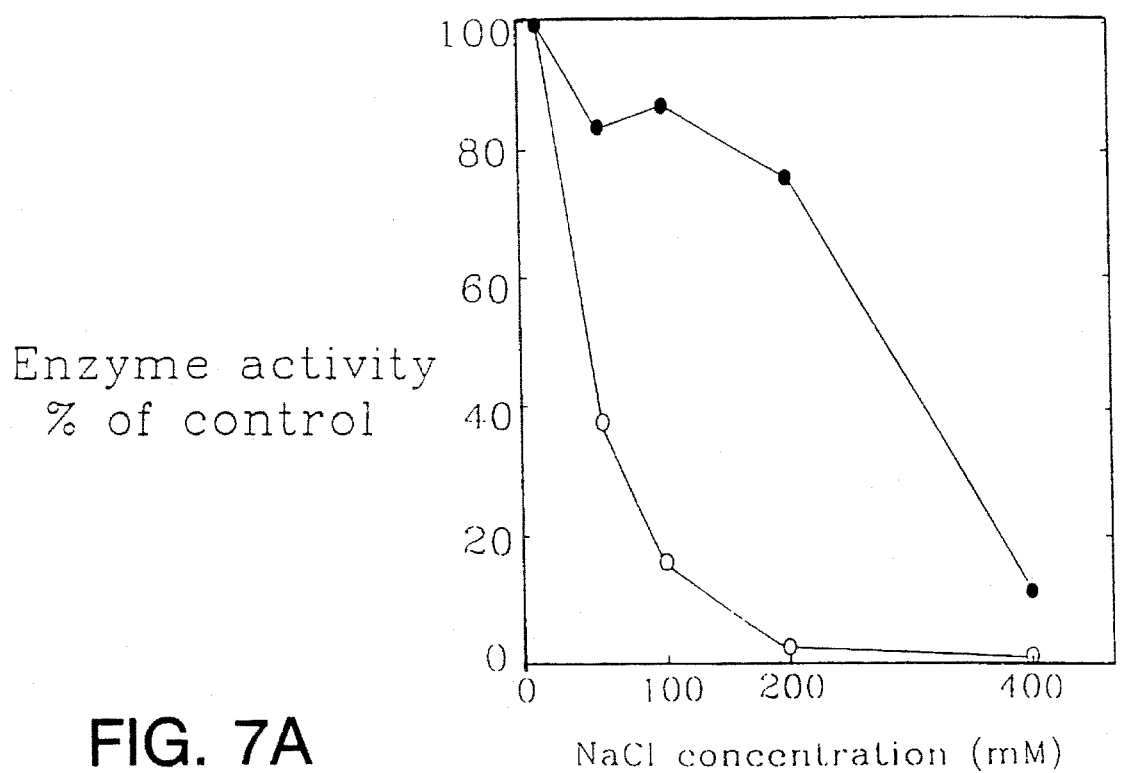
Figure 7C:
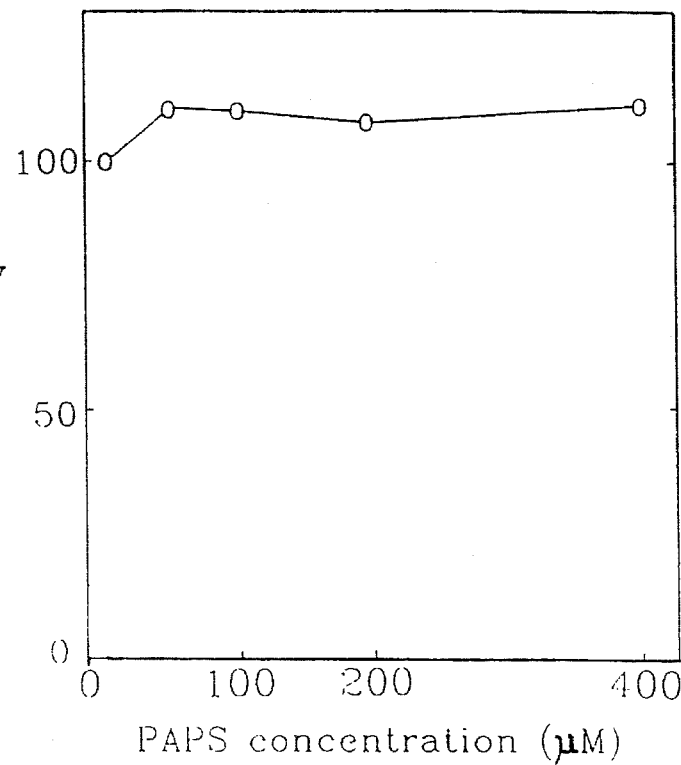
Figure 7B:
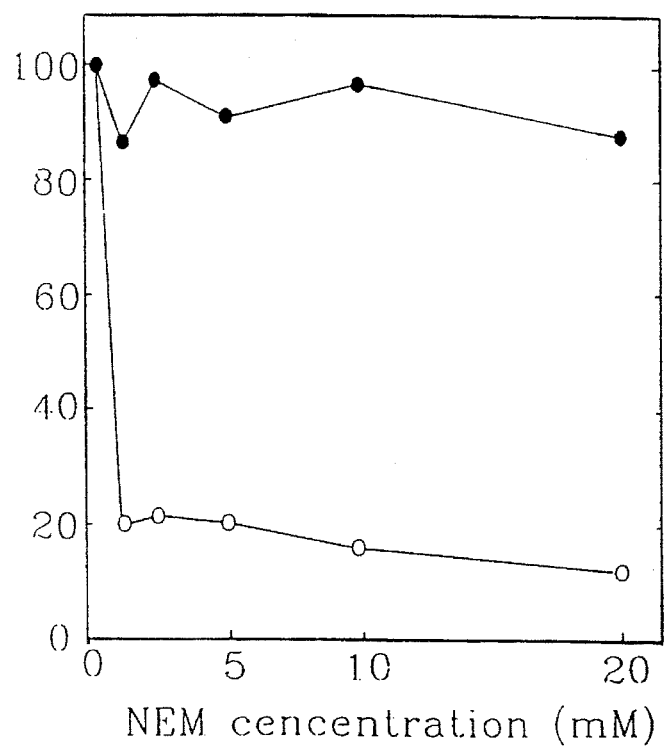
Figure 7D:
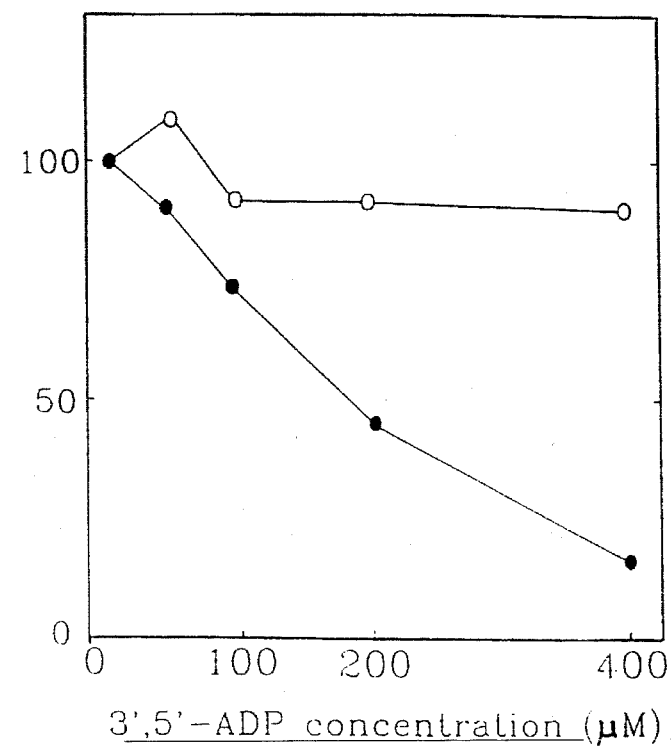

FIG. 7A depicts the sensitivity of the sulfotransferase and deacetylase activities of N-HSST to NaCl; FIG. 7B depicts the sensitivity of activities to the sulfotransferase and deacetylase activities to NEM; FIG. 7C depicts the dependence of N-deacetylase activity on PAPS; FIG. 7D depicts the sensitivity of the sulfotransferase and deacetylase activities of N-HSST to 3',5'-ADP. N-sulfotransferase activity, (●); N-deacetylase activity, (○).

There now follows a description of the large scale purification of rat liver N-heparan sulfate sulfotransferase (N-HSST), the cloning and characterization of the N-HSST gene, the overexpression of the recombinant N-HSST protein and the characterization of the enzymatic activities of the recombinant N-HSST.

Purification and Amino Acid Sequencing of N-Heparan Sulfate Sulfotransferase Tryptic Peptides Initially, small scale purification of rat liver N-heparan sulfate sulfotransferase (N-HSST) was carried out as described in Brandan and Hirschberg (*J. Biol. Chem.* 263:2417, 1988). The enzyme preparation isolated by this approach represented a 5.5% yield and exhibited a specific activity of 0.9 U/mg.

In order to obtain a yield and enzyme activity sufficient for ready generation of peptides for amino acid sequencing, N-HSST purification was scaled up as follows. A total of 7.5 kg of frozen rat liver was used as starting material, and purification was carried out on three batches of 2.5 kg each. Each batch was homogenized (as described in Brandan and Hirschberg; supra) in Buffer A (i.e., 10 mM Hepes, pH 7.2, 10 mM MgCl$_2$, 0.1% Triton X-100) containing a cocktail of protease inhibitors (specifically, 5 µM Nα-p-tosyl-L-lysine chloroethyl ketone, 3 µM N-tosyl-L-phenylalanine chloroethyl ketone, 3 µM phenylmethylsulfonyl fluoride, all purchased from Sigma, St. Louis, Mo., and 3 µM Pepstatin A, Peptides International, Inc., Louisville, Ky.). A tissue extract was obtained, applied to a 2.6 L DEAE-Sephacel column and eluted, all as described in Brandan and Hirschberg (supra). The eluate was then applied to a 0.5 L heparin agarose column and eluted with Buffer A containing 0.70M NaCl. Because of the large eluate volume, the material could not be subjected directly to dialysis (as previously described in Brandan and Hirshberg, supra), but was instead concentrated following five passages through a Minitan ultrafiltration apparatus (Millipore Corporation, Bedford, Mass.). Because the application of the material to a 3',5'-ADP-agarose column as described in Brandan and Hirschberg (supra) was also found to be unsuitable (as determined by pilot studies), the Minitan preparation was instead adjusted in Buffer A to a final concentration of 10 mM NaCl and 8% glycerol and was applied to a 120 ml 3',5'-ADP-agarose column. The enzyme eluted at a salt concentration of 30 mM NaCl and 8% glycerol, a concentration which was considerably lower than that used to elute the enzyme in the small scale purification described above. The eluted material was dialyzed, again concentrated in a Minitan apparatus, and applied in Buffer A containing 8% glycerol to a second 3',5'-ADP-agarose column (50 ml). The column was washed with Buffer A containing 12 mM NaCl and 8% glycerol. The enzyme was eluted with Buffer A containing 12 mM NaCl, 8% glycerol, and 0.25 mM 3',5'-ADP (again, a considerably lower salt concentration than was necessary for the small scale purification). The three batches of enzyme derived from the large scale purification were combined and applied to a 10 ml wheat-germ Sepharose column, and fractions were eluted as generally described in Brandan and Hirschberg (supra).

The N-HSST protein preparation obtained by this procedure represented a 20% yield and exhibited an enzyme activity of 10 U/mg, a 4-fold higher yield and 10-fold higher specific activity than was obtained using the published Brandan and Hirschberg procedure.

Polyacrylamide gel electrophoresis (PAGE) revealed a putative N-HSST band at 97 kD. To determine whether this band actually represented the N-HSST protein, a small aliquot was eluted from the wheat-germ Sepharose column and was subjected to hydroxylapatite column chromatography. Specifically, the enzyme was applied to a bio-gel HPHT column (100×7.8 mm) (Bio-Rad, Rockville Center, N.Y.) in 1 mM sodium phosphate, pH7.2, 10 mM MgCl$_2$, 154 µM NAN$_3$, 2% glycerol, 0.1% Triton X-100, and the above-described cocktail of protease inhibitors, and eluted with a linear gradient of sodium phosphate beginning at 1 mM and ending at 100 mM. Fractions of 1 ml were collected and assayed for enzyme activity. Fractions 8–12 exhibited enzyme activity; radioiodination followed by SDS-PAGE revealed that a major broad band at 97 kD correlated with enzyme activity.

Some heterogeneity in the 97 kD band was apparent. To determine whether this heterogeneity was due to carbohydrate modification, radioiodinated bands were cut out of the polyacrylamide gel (above) and subjected to N-glycanase treatment by standard techniques. Following such treatment, the proteins in each fraction were found to have the same mobility (as determined by SDS-PAGE and autoradiography). Moreover, each protein was found to have an apparent molecular weight of 85 kD, suggesting that the N-HSST was an N-linked glycoprotein and that the protein might contain O-linked sugars.

The homogeneity of the protein backbone was established by peptide mapping analysis. Protein from the above fractions was subjected to digestion with S-protease V8 or chymotrypsin and subjected to 15% SDS-PAGE electrophoresis and autoradiography. Virtually identical protein patterns were obtained for each fraction. Radioiodinated protein in the 97 kD area was also prepared for the enzyme fraction eluting off the wheat-germ Sepharose column. Following protease treatment (as described above), the peptide pattern obtained for the Sepharose-purified enzyme was the same as that obtained for the hydroxylapatite-purified enzyme. Based on these experiments, it was concluded that the protein migrating in the 97 kD range following wheat-germ Sepharose column chromatography was of sufficient purity for peptide sequencing.

Accordingly, approximately 100 μg of the partially purified N-HSST which had been eluted from the wheat germ Sepharose column was subjected to 7% SDS-PAGE (in 9 lanes) and then transferred electrophoretically to nitrocellulose (at 300 mA for 1 h) in 25 mM Tris, 195 mM glycine buffer containing 10% methanol. Protein bands were stained with Ponceau S (Sigma Chemical Co., St. Louis Mo.). The band migrating at the 97 kD area was excised for subsequent analysis. Following solid-phase trypsin digestion according to Aebersold et al. (*Proc. Nat. Acad. Sci.* USA 84:6970–6974, 1987), but without the NaOH wash, tryptic peptides were fractionated by reverse-phase HPLC as previously described (Lopez-Casillas, F., et al., *J. Cell* 67:785–795, 1991) and selected for automated Edman degradation according to strategies outlined by Lane et al. (*J. Prot. Chem.*, 10:151–160, 1991). Table I shows the amino acid sequence obtained for the different tryptic peptides.

TABLE I

AMINO ACID SEQUENCE OF TRYPTIC PEPTIDES OF THE RAT LIVER N-HEPARAN SULFATE SULFOTRANSFERASE

| Peptide Number | Amino Acid Sequence* |
| --- | --- |
| 1 | SANYFDSEVAPR (SEQ ID NO: 6) |
| 2 | DHNIELSK (SEQ ID NO: 7) |
| 3 | AHDDPVALK (SEQ ID NO: 8) |
| 4 | FFHTGTDAEDAGD (SEQ ID NO: 9) |
| 5 | ANENSLLSAQLK (SEQ ID NO: 10) |
| 6 | VTSTEEYPHLKPA(R) (SEQ ID NO: 11) |
| 7 | DIWSK (SEQ ID NO: 12) |
| 8 | MKG(V)EDVK (SEQ ID NO: 13) |
| 9 | MGQTLP (SEQ ID. NO: 14) |
| 10 | SSESIPHLTADAGL (SEQ ID NO: 15) |
| 11 | YILVDIDDIFVGK (SEQ ID NO: 16) |

*Amino acids within parentheses are tentative identifications.

Oligonucleotides and Polymerase Chain Reaction

Tryptic peptides 1 (SEQ ID NO:6), 2 (SEQ ID NO:7) and 3 (SEQ ID NO:8) (Table I) were used to design degenerate oligonucleotide primers (sense or antisense; SEQ ID NOS: 2, 3, 4, and 5) with deoxyinosine substitution as shown in FIG. 1A, which were then used to amplify interpeptide encoding sequences by PCR from rat liver single-strand cDNA (see below). The PCR reaction was carried out as previously described by Lee et al. (*Science,* 239:1288–1291, 1988) in a final volume of 50 μl containing 0.4 μM of each primer oligonucleotide, 10–40 ng of the first-strand cDNA library as template, 1.25 units of Taq polymerase (Perkin Elmer/Cetus, Norwalk, Conn.); and 50 μl of mineral oil. Samples were placed in an automatic heating/cooling block, programmed for 35 temperature-step cycles of 92° C. (1.5 min), 50° C. (2 min), and 72° C. (5 min), with a final 10 minute extension at 68° C.

Reaction products were analyzed by agarose gel electrophoresis. Sequencing of the PCR products was performed according to Maxam and Gilbert (Maxam and Gilbert, *Meth. Enzymol,* 65:499–560). Briefly, one primer was end-labelled with [γ-$^{32}$P]ATP (Dupont, NEN Research Products, Boston, Mass.) and T$_4$ polynucleotide kinase (Pharmacia, Piscataway, N.J.). Products generated by PCR, using the labelled primer, were then separated on 7% PAGE and localized by autoradiography. The appropriate band was cut out from the gel, eluted and subjected to sequencing.

Figure 1B:
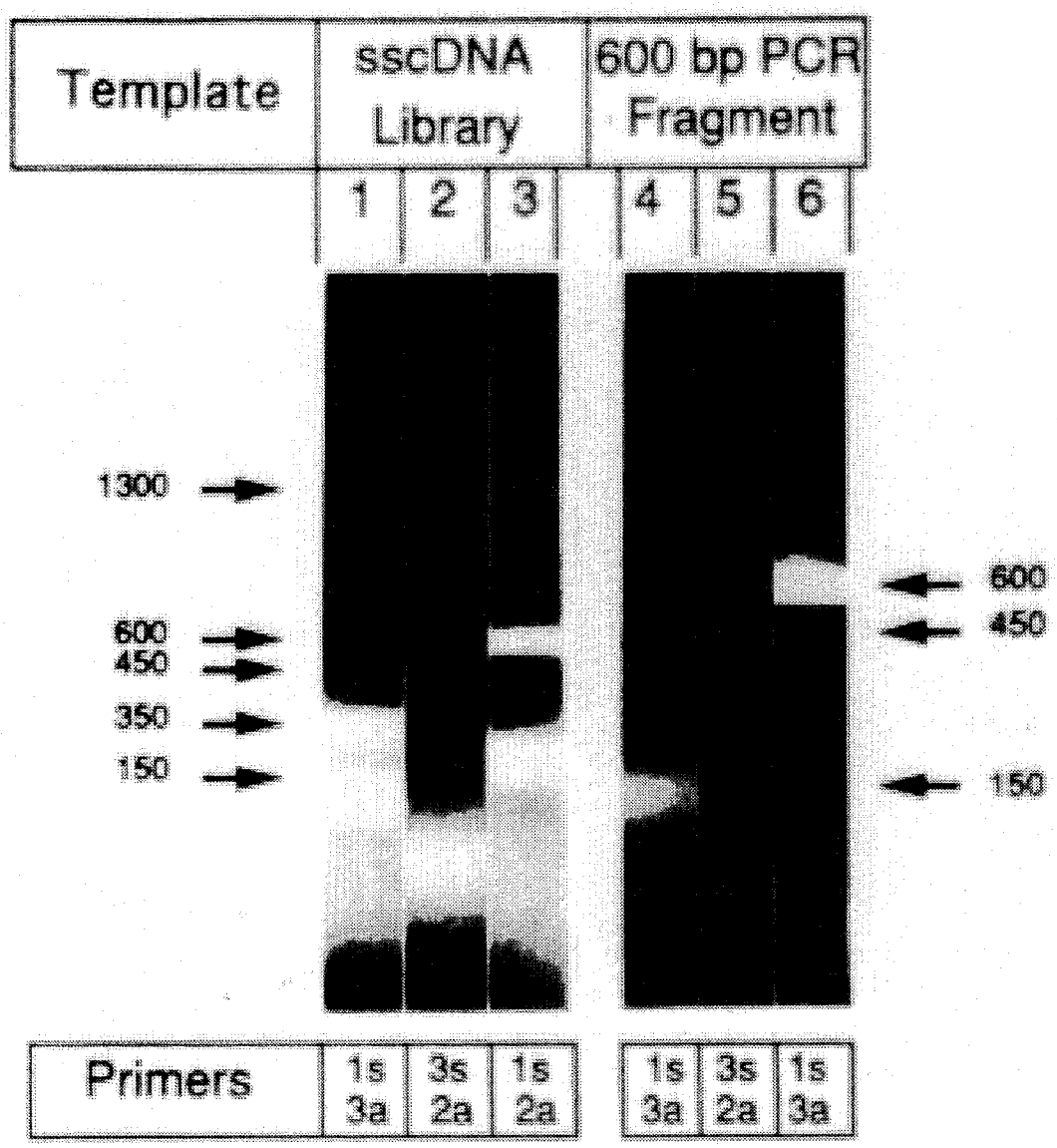
Figure 1C:
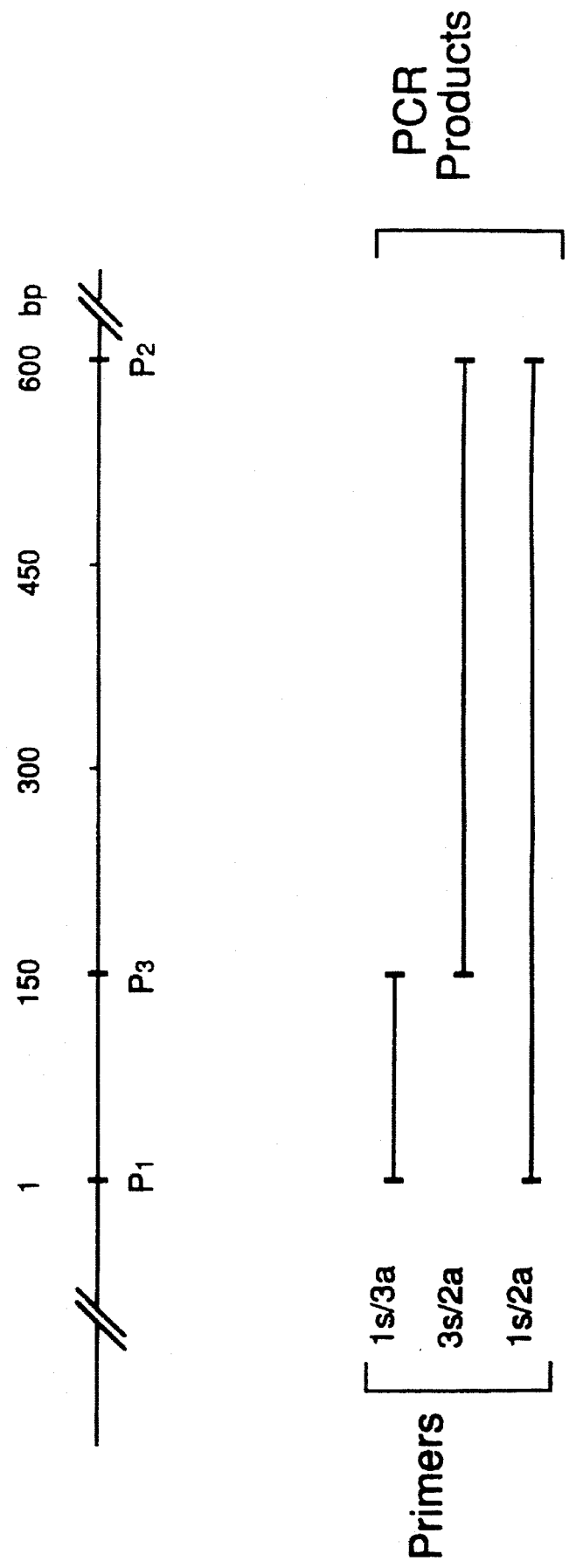

When primers 1-sense (1s; SEQ ID NO:2) and 2-antisense (2a; SEQ ID NO:3) (FIG. 1A) were used in a PCR using a rat liver single-stranded cDNA library as the template, fragments of 250, 600, and 1300 bp were obtained (FIG. 1B, lane 3). It was determined that the 250 and 350 bp products lacked the nucleotide sequence encoding the three carboxy-terminal amino acids of peptide 1 (Ala, Pro, Arg; FIG. 1A). PCR using primers 3s (SEQ ID NO:4) and 2a (SEQ ID NO:3) resulted in a 450 bp fragment (FIG. 1B, lane 2), while PCR with primers 1s (SEQ ID NO:2) and 3a (SEQ ID NO:5) produced a 150 bp fragment (FIG. 1B, lane 1). These fragments appear to be the PCR products which would be predicted from a hypothetical alignment of the peptides as shown in FIG. 1C. Further proof for this alignment was obtained by using the 600 bp PCR fragment as template with a combination of primers 3s (SEQ ID NO:4) and 2a (SEQ ID NO:3) and 1s (SEQ ID NO:2) and 3a (SEQ ID NO:5). As shown in FIG. 1B, the 450 bp fragment was amplified with primers 3s (SEQ ID NO:4) and 2a (SEQ ID NO:3) (lane 5) and the 150 bp with primers 1s (SEQ ID NO:2) and 3a (SEQ ID NO:5) (lane 4). Finally, the 600 bp fragment was sequenced and found to contain nucleotide sequences adjacent to primer 1s (SEQ ID NO:2) encoding for the three carboxyterminal amino acids of peptide 1 (SEQ ID NO:6) (Ala, Pro, Arg; FIG. 1A). In addition, sequences encoding peptide 2 (SEQ ID NO:7) were found, as predicted, 150 bp from the 5' end.

Construction of a λgt10 Library

Total RNA was prepared from rat liver according to Chirgwin et al. (*Biochem.* 18:5294–5299). Poly(A)$^+$ RNA was purified by oligo(dT) cellulose column chromatography (Konarska, *Cell* 38:731–736, 1984). Ten μg of poly(A)$^+$ RNA were used to synthesize a first strand cDNA library using murine leukemia virus reverse transcriptase and oligo(dT) primers from BRL (Gaithersburg, Md.). One aliquot of the first-strand cDNA library was used as template in the PCR reactions. Another aliquot was used to synthesize the second strand and the resultant double-stranded CDNA was ligated to λgt10 arms using a kit from BRL. This λgt10 library (which was not further amplified) was then packaged in vitro using a λ DNA packaging kit from Stratagene (LaJolla, Calif.).

Screening of λgt10 and λZAP Libraries

Phage from the λgt10 library, obtained as described above, were used to infect host strain *E. coli* C-600 and plated at 2–3×10$^4$ PFU/150 mm dish. Phage from an amplified λZAP library (K. Moremen, Univ. of Georgia) were used to infect the host strain *E. coli* XL-1 Blue and plated at 2–3×10$^4$ PFU/150 mm dish. In both cases, approximately 8×10⁵ plaques were screened as described by Sambrook et al. (Sambrook et al., *Molecular Cloning, a Laboratory Manual*, Cold Spring Harbor Laboratory Press, 2.109–2.117). One positive clone was obtained from the λgt10 library (H2a) and two different positive clones were obtained from the λZAP library (J1a and J3).

DNA Sequence Analysis

Figure 2:
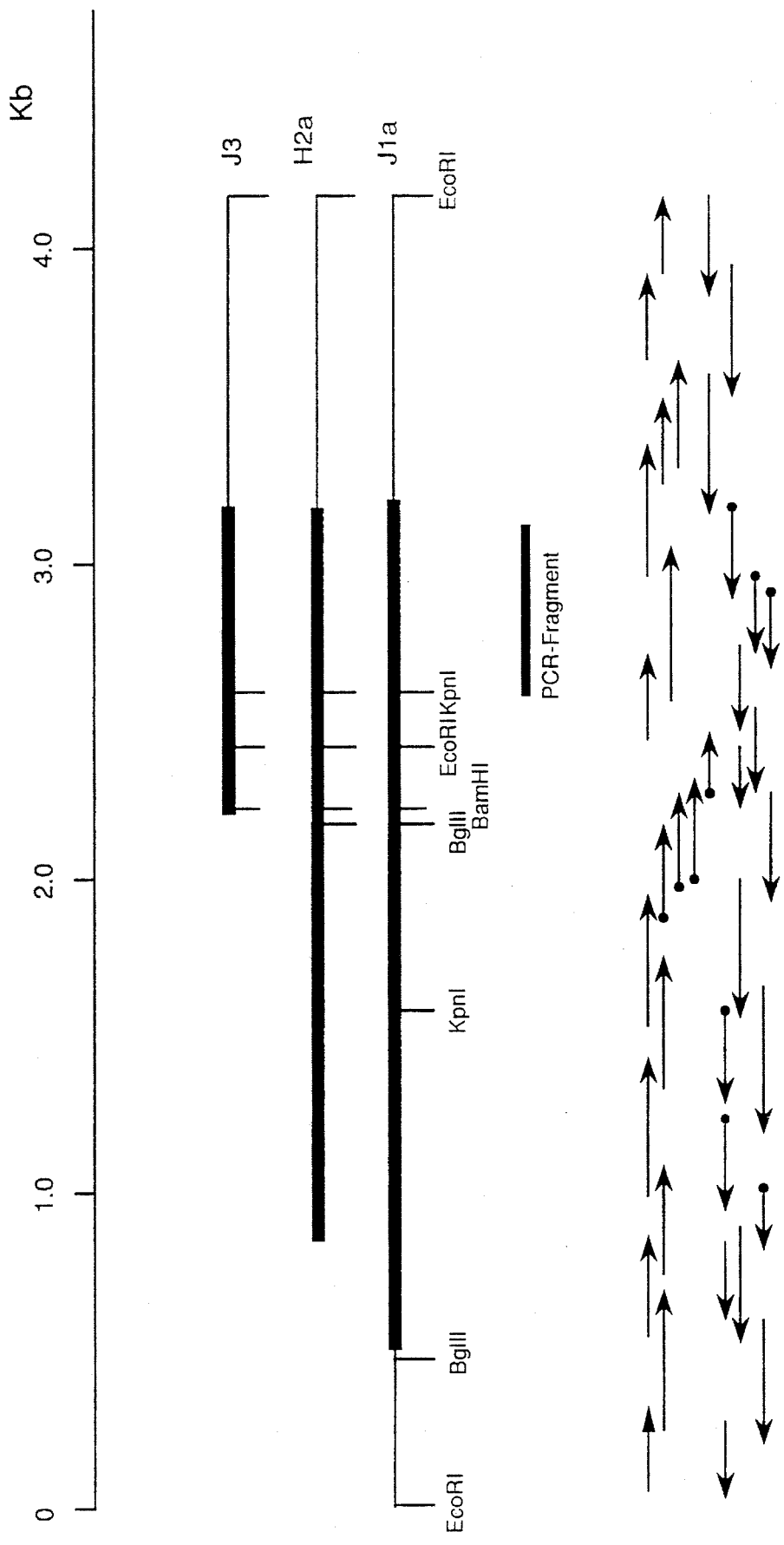
FIG. 2 is a schematic representation of the rat N-heparan sulfate sulfotransferase cDNA clones and sequencing strategy.

DNA from the λgt10 positive clone (H2a) was isolated and digested with the restriction endonuclease EcoRI, releasing two 1.7 kb fragments from the cDNA insert. These fragments were inserted in both orientations into M13mp18, generating four different M13 clones. Positive clones J1a and J3, derived from lambda ZAP, were processed as described in the Stratagene protocol for the excision of the Bluescript 5K-plasmid containing the cDNA inserts. One of the clones (J1a) was cut with EcoRI, producing 4 fragments of 1.0, 1.3, 1.7 and 2.4 kb. All of these fragments were subcloned into M13mp18. Sequencing was performed according to Sanger et al. (*Biochem.* 74:5463, 1977) by the dideoxytermination method using deoxyadenosine 5'α-[$^{35}$S]triphosphates and Sequenase (United States Biochemical, Cleveland, Ohio). Part of the sequences of each M13 clone was obtained by generation of single strand deletion fragments using the exonuclease activity of the T4 DNA polymerase according to the Cyclone I Biosystem (International Biotechnologies, New Haven, Conn.). Part of the sequence of J1a and J3 were also obtained by double strand sequencing. All the other sequences were obtained by use of the M13 universal primer and/or specific primers. A partial restriction map and the strategy used to sequence the cDNA are shown in FIG. 2. The horizontal arrows represent the direction and extent of each sequencing reaction; closed circles indicate sequences obtained from deletion mutants generated by T4 polymerase exonuclease digestion.

Predicted Nucleotide and Amino Acid Sequence of the N-Heparan Sulfate Sulfotransferase The nucleotide sequence of the N-HSST cDNA, as determined by analysis of three independent clones, is shown in FIGS. 3A to 3F (SEQ ID NO:1). The locations of the 11 tryptic peptide sequences obtained after digestion of the purified N-heparan sulfate sulfotransferase are underlined with a double solid line; the putative uncleaved, transmembrane hydrophobic domain is shown within a box; the possible sites for N-glycosylation sites are shown with a black dot. The single open reading frame predicts a protein of 882 amino acid residues with a molecular mass of 100,777 daltons with a single transmembrane domain from amino acid residues 18–39. Support for the methionine codon indicated at position 1 being the correct initiation site is provided by the facts that it is the first ATG of the longest open reading frame and also by the presence of a purine at position −3, the most critical residue in the initiation sequence (Kozak, *J. Cell. Biol.* 108:229, 1989). In addition, there are three different stop codons upstream from the proposed initiation site at positions −216, −231, and −285.

The characteristics derived from the predicted protein sequence are in agreement with the previous results obtained from the purified protein; the apparent molecular weight estimated by SDS-PAGE and sucrose sedimentation (97 kD) (Brandan and Hirschberg, supra) is close to the value predicted by the amino acid sequence. Secondly, four potential sites of N-glycosylation are located in the sequence; previously, the N-HSST was found to be a membrane-bound protein which is N-glycosylated (Brandan and Hirschberg, supra). Finally, all the tryptic peptide sequences which had been obtained from the purified protein were found in the predicted protein sequence, confirming that the cDNA clones encode the purified N-HSST.

The predicted sequence derived from the cDNA shows that the rat liver N-HSST is a type II membrane protein. Comparison with other Golgi proteins which appear to be similar types of membrane proteins reveals, in all cases, a short cytosolic hydrophilic domain followed by a hydrophobic domain which usually serves as an uncleaved signal sequence-anchor followed by a large hydrophilic domain which faces, presumably, the lumen of the Golgi apparatus.

The 5' untranslated region appears to be rather long; and is relatively rich in GC (60%). Before the ATG which codes for the initial Met of the longest open reading frame encoding the purified protein, there are two ATG codons in a different reading frame; however, immediately after these ATG there is a stop codon in frame. Moreover, the presence of a purine in position −3 supports the hypothesis that ATG in position 1 in FIG. 3A is the first codon (Kozak, *J. Cell. Biol.*, 108:229–241, 1989.)

Expression of the N-Heparan Sulfate Sulfotransferase cDNA in COS-1 Cells

Direct evidence demonstrating that the isolated cDNA encodes the N-HSST protein was obtained by expressing the cDNA in COS-1 cells as follows.

To construct the plasmid containing the N-HSST cDNA termed pCMVST, a Hind III fragment containing the open reading frame of 2546 bp was excised from the J1a clone and ligated into the Hind III site of the pCMV5 expression vector (Anderson et al., *J. Biol. Chem.* 264:8222–8229, 1989). DH-5α cells were transformed with the ligation mixture and plated on LB ampicillin plates. Recombinant plasmids were analyzed by restriction mapping to confirm the correct orientation of pCMVST inserts.

For transfection, monolayer cultures of COS-1 cells were grown on 100 mm culture dishes in an incubator at 37° C. in 5% $CO_2$ with 10% DMEM (Gibco-BRL, Gaithersburg, Md.) containing 100 U/ml penicillin (Sigma Chemical Co., St. Louis, Mo.), 100 µg/streptomycin (Sigma Chemical Co.), 0.25 µg/ml amphotericin B (Sigma Chemical Co.), and 10% fetal calf serum (JR Scientific, San Francisco, Calif.). When the cells were nearly 60–70% confluent they were transfected with either pCMVST, expression vector alone (pCMV5), or with pCMV5 Glut-1, a recombinant plasmid, containing an insert that encodes the sequence of the glucose transporter. The transfection was performed using the DEAE-dextran method (Aruffo, *Current Protocols in Molecular Biology*, Suppl. 14, Unit 16.13, 1991). Briefly, 5 ml of DMEM containing 10% Nu serum (Collaborative Biomedical Products) were mixed with 0.2 ml of a solution of PBS containing 10 mg/ml DEAE-dextran plus 2.5 mM chloroquine. Fifteen µg of the relevant plasmid were then added and the solution applied to the cells. After a 4 h incubation, the medium was replaced with 5 ml of 10% DMSO in PBS, incubated for 2 min at room temperature and then replaced with 25 ml of 10% DMEM containing 100 U/ml penicillin, 100 µg/ml streptomycin, 0.25 µg/ml amphotericin B and 10% fetal calf serum. The cells were then incubated for 65 hours, washed with DMEM alone, collected by scraping, and homogenized with a Dounce homogenizer in the presence of 0.2M Sucrose, 10 mM Tris-HCl, pH 7.8 and 0.2 mM EDTA. N-HSST activity was measured in 20 µl of homogenate as previously described (Brandan and Hirschberg, supra). All experiments which involved N-HSST were done in triplicate; experiments which involved sialyl transferase were done in duplicate.

As shown in Table II, when the vector containing the isolated cDNA was used, N-HSST activity in the transfected cells was 8–10 fold above that of control transfections. This increase in activity was specific because no increase in sialyltransferase activity was seen in the same cells. These results, therefore, demonstrate that the isolated cDNA encodes a protein with N-HSST activity and most likely the enzyme catalyzing this reaction in vivo.

TABLE II

OVEREXPRESSION ON N-HEPARAN SULFATE SULFOTRANSFERASE IN COS-1 CELLS

| PLASMID | PLATE 1 | | PLATE 2 |
|---|---|---|---|
| | N-HSST pmol/mg/min | Sialyl-T* cpm/mg/min | N-HSST pmol/mg/min |
| None | 19.0 ± 2.9 | nd | 20.7 ± 1.5 |
| pCMV5 | 19.9 ± 1.4 | 5330 | 20.7 ± 1.9 |
| pCMVGT | 18.5 ± 0.5 | nd | 20.5 ± 0.7 |
| pCMVST | 178.5 ± 17.6 | 2910 | 165.3 ± 11.5 | nd = not determined.

Northern Analysis

A Northern blot of poly(A$^+$) RNA from rat liver was prepared and hybridized with a single-stranded probe containing the 3' end of the coding sequences follows.

RNA was denatured in a solution of 50% formamide (vol/vol), 6% formaldehyde (vol/vol), 20 mM MOPS, pH 7.0 at 65° C., separated by gel electrophoresis in a 1.2% agarose gel containing 6% formaldehyde (vol/vol) and transferred to a Hybond N$^+$ nylon membrane (Amersham, Chicago, Ill.) for 18 h. The RNA was fixed by baking at 80° C. for 2 h and then prehybridized for at least 2 h at 65° C. in 6× SSPE (1×=NaCl: 8.765 g/L; NaH$_2$PO$_4$:1.38 g/L; EDTA: 0.37 g/L; pH 7.4), 5× Denhardt's solution (1×=Ficoll: 0.2 g/L; bovine serum albumin: 0.2 g/L; polyvinylpyrrolidone: 0.2 g/L), 0.5% SDS and 100 µg/ml of denatured salmon sperm DNA. A single stranded probe was prepared as described by Church and Gilbert (*Proc. Nat. Acad. Sci.*, 81:1991–1995, 1984) using as a template the M13 subclone containing the 1.7 kb EcoRI fragment derived from clone H2a. A specific 20mer oligonucleotide with the following sequence was used as primer: 5' CTGTGGTGCCTGTTTTCTGG 3' (SEQ ID NO: 17). The hybridization was carried out with the probe (4×10$^6$ cpm/ml) for 15–18 h at 65° C. in the same solution, and then washed at room temperature in 2× SSC, 0.1% SDS and finally, in 0.1× SSC, 0.1% SDS at 65° C. The membrane was subjected to autoradiography overnight at −70° C. using intensifying screens.

Figure 4:
FIG. 4 is a representation of a Northern analysis of poly(A)$^+$ RNA from rat liver.

As can be seen in FIG. 4, three bands with a relative size of 8.5, 7.0, and 4.2 kb were clearly seen, the larger one being more abundant than the smaller ones. The same bands were also seen with less intensity when 40 µg of total RNA was used.

The size of the cloned cDNA comprising the complete sequence of the N-HSST is around 4.1 kb which is close to the 4.2 kb size of one of the mRNA observed in Northern analyses. The intense 8.5 kb band also observed in Northern analyses suggests that a large unprocessed species of mRNA is produced by the genomic DNA which encodes N-HSST.

The modification reactions involved in the biosynthesis of sulfated glycosaminoglycans are closely coupled. We therefore decided to investigate whether or not N-HSST was capable of catalyzing any modification of heparin or heparan sulfate other than N-sulfation by examining recombinantly-derived full-length and soluble forms of N-HSST produced by transient expression in COS cells.

Construction of a Plasmid Encoding a Soluble Form of N-HSST

A soluble form of the N-HSST corresponding to amino acids 42–882 of the full-length, transmembrane molecule fused at its amino terminus to a portion of Protein A was produced by use of the polymerase chain reaction. For this purpose, 30 pmol each of the primers 5'-GGTGTCGA-CACTCGAGCCCTCGGCAGATG-3' (SEQ ID NO:18) and 5'-GGCGTCGACCAAGCGTTCTGGCTGGCTGTG-3' (SEQ ID NO:19) were added to 10 ng of pCMVST DNA in a total volume of 100 µl containing 10 mM Tris-HCl, pH 8.3, 50 mM KCl, 1.5 mM MgCl$_2$, 0.01% gelatin, 100 µmol of each dNTP, and 2.5 units Amplitaq (Perkin Elmer-Cetus, Norwalk, Conn.). The following amplification protocol was followed: one cycle at 95° C. for 5 min; thirty-five cycles at 95° C. for 45 sec, 55° C. for 30 sec, and 72° C. for 3 min; and one cycle of 72° C. for 10 min. The product was digested with SalI, agarose gel purified, and ligated into the eukaryotic expression vector, pRK5F10Protein-A, derived from the Protein A-encoding vector, pPROTA (Sanchez-Lopez et al., *J. Biol. Chem.* 263:11892–11899, 1988).

Transient Expression of Full Length and Soluble N-HSST cDNA in COS Cells and purification of soluble N-HSST COS cells (5×10$^5$ cells/10 cm dish) were transfected with 5 µg of pCMVST DNA containing the cDNA encoding the full-length transmembrane N-HSST or pCMV5 vector DNA alone (control) in a 10 cm dish using the DEAE-dextran transfection method (Seed and Aruffo, *Proc. Natl. Acad. Sci. USA* 84:3365–3369, 1987; Aruffo and Seed, *Proc. Natl. Acad. Sci. USA* 84:8573–8577, 1987). After 72 hours of incubation, the monolayers were rinsed, scraped of the dishes, and collected by centrifugation. Cell pellets were resuspended in homogenate buffer (250 mM sucrose, 1 µg/ml leupeptin, 0.4 µg/ml pepstatin, 0.2 mM phenylmethylsufonyl fluoride, and 50 mM Tris-HCl, pH 7.5), and disrupted by a Dounce homogenizer (20 strokes). To purify and immobilize the soluble N-HST on IgG-agarose, media (10 ml) from one dish of cells transfected with the plasmid containing the soluble N-HSST was collected 72 hr after transfection and incubated with 10 µl of rabbit IgG-agarose (Sigma, St. Louis, Mo.) at 4° C. for 24 hr. To elute the enzyme from the IgG-agarose, the beads (10 µl) were washed with 10 ml of 50 mM Tris-HCl, pH 7.4, 20% glycerol, and incubated with 500 µl of 100 mM citrate buffer, pH 4.0, vortexed for 10 sec, centrifuged, and the supernatant fluid was neutralized with 20 µl of 1M Tris- HCl, pH 8.2, 20% glycerol. The preparation was adjusted to a final concentration of 20% glycerol and stored at −20° C. The purity of these preparations was assayed by SDS-PAGE using a silver stain method for detection.

N-Deacetylase and N-Sulfotransferase Assays

N-deacetylase activity was measured by determining the release of [$^3$H]acetate from N-[$^3$H]acetylated-polysaccharide derived from *E. coli* K5-derived capsular polysaccharide with a specific activity of 400 cpm/ng (dry weight) after 1 hour incubation as described (Bame et al., *J. Biol. Chem.* 266:12461–12468, 1991). N-Sulfotransferase and O-sulfotransferase activities were measured by determining $^{35}SO_4$-incorporation into N-desulfated heparin and completely desulfated, N-resulfated heparin, respectively, from PAP$^{35}$S after a 30 min incubation as described (Ishihara et al., *Anal. Biochem.* 206:400–407, 1992). Twenty five µg of total protein from each cell homogenate was included in the enzyme reactions.

Affinity Chromatography

Ten µg of purified soluble enzyme was loaded onto a 1 ml 3',5'-ADP-agarose (Sigma, St. Louis, Mo.) column equilibrated with buffer A (50 mM Tris-HCl, pH 7.5, 20% glycerol and 50 mM NaCl). The column was washed with 10 ml buffer A. Elution was accomplished with buffer containing an eight step gradient of 3',5'-ADP (0–400 μM) Fractions of 200 μl were collected and 5 μl of each was assayed for both enzymatic activities. Conditions for the WGA-sepharose column (Pharmacia, Piscataway, N.J.) were identical except that buffer A additionally contained 0.15M NaCl, and elution was initiated with a step gradient of N-acetylglucosamine (0–400 mM).

Results

Transfection of COS cells with a vector encoding the full length, membrane-bound form of N-HSST resulted in substantial increase (over control) in both N-sulfotransferase and N-deacetylase activities from cell extracts (Table 1). No increase in O-sulfotransferase activity was detected (Table 1).

TABLE 1

Overexpression of N-HSST in COS cells

| | N-deacetylase activity $^3$H released (cpm) | N-Sulfo- transferase activity $^{35}$S incorporated (cpm) | O-sulfo- transferase activity $^{35}$incorporated (cpm) |
|---|---|---|---|
| N-HSST transfected COS cell extract | 52,000 | 61,000 | 8,900 |
| Control COS cell extract | 8,200 | 18,200 | 9,100 |
| Soluble N-HSST- IgG-agarose | 59,000 | 82,500 | N.D. |
| Control IgG-agarose | 860 | 750 | N.D. |

N.D.; not determined
Transfected COS cell extracts were prepared and N-deacetylase, N-sulfotransferase, and O-sulfotransferase activities in each cell extract were measured as described in Materials and Methods. The soluble enzyme was isolated using 10 μl of rabbit IgG-agarose to bind the enzyme derived from the culture medium (10 ml) of one dish of transfected cells. The enzyme was used while still immobilized to the IgG-agarose. IgG-agarose exposed to an equivalent amount of media from cells transfected with a plasmid containing the insert for the soluble enzyme in the reverse orientation served as the control. All of the determinations are the average values obtained from a minimum of duplicate cultures.

To directly examine if both activities were derived from the recombinant protein, a plasmid was constructed to facilitate purification of N-HSST, following transfection. This plasmid DNA encoded for a soluble protein consisting of the predicted Golgi-lumenal portion of the N-HSST fused at its amino terminus to the IgG binding portion of Protein-A. As expected, the majority of this soluble N-HSST produced by COS cells was secreted into the culture medium allowing for its purification by affinity chromatography on IgG-agarose. The purified protein migrated as a single species at 130 kDa (FIG. 1). The apparent molecular weight of the soluble protein agreed with that expected based on the open reading frame encoded by the plasmid DNA. The immobilized soluble protein also displayed both the N-deacetylase and N-sulfotransferase enzymatic activities (Table 1).

To eliminate the possibility that a small molecular weight cofactor was required for either of these enzymatic activities, a series of experiments were executed. The enzymatic properties and SDS-PAGE profile of soluble N-HSST, immobilized on IgG-agarose beads, were unaffected by successive treatments with 0.5M NaCl, 0.2M EDTA, and 1% Triton X-100. Furthermore, alterations in either enzymatic activity were not observed after the treated protein was eluted from the IgG-agarose and then dialyzed in a 30 Kda molecular weight cut-off membrane to remove small molecules.

The eluted soluble enzyme was also subjected to two chromatographic procedures previously utilized for the purification of the full length, transmembrane form of N-HSST. Both activities bound to and were coeluted from a 3',5'-ADP agarose column and a wheat germ agglutinin (WGA)-sepharose column (FIG. 2). Again, no change was seen in the migration of the protein by SDS-PAGE analysis.

The chromatographic properties of the soluble N-HSST were also observed for the full length, transmembrane form of the N-HSST partially purified from a transfected COS cell-derived extract. This excluded the possibility that the Protein-A portion of the soluble enzyme might be serving as a cofactor for the N-deacetylase activity. These results, taken together, demonstrate that a single protein possesses both enzymatic activities independent of other proteins or cofactors. Thus, it would be more appropriate to designate this enzyme as a heparan sulfate-N-deacetylase-N-sulfotransferase (HS-NdAC-NST).

The sensitivity of either the sulfotransferase or deacetylase activity to N-ethylmaleimide (NEM), NaCl, 3',5'-ADP, and adenosine 3'-phosphate, 5'-phosphosulfate (PAPS) were also studied using purified soluble HS-NdAC-NST, as shown in FIGS. 7A to 7D. The N-deacetylase activity was very sensitive to NaCl, with a loss of greater than 90% of the activity at physiological concentrations. A significant loss in N-sulfotransferase activity was seen only at concentrations greater than 200 mM. NEM inhibited 80% of the N-deacetylase activity at 1 mM concentration, while the N-sulfotransferase was unaffected at all concentrations tested (up to 20 mM). The N-sulfotransferase activity was inhibited by 3',5'-ADP (FIG. 7D), in agreement with previous results obtained with the heparin-related mast cell-derived enzyme (Pettersson et al., *J. Biol. Chem.* 266:8044–8049, 1991; Reisenfeld et al., *J. Biol. Chem.* 255:922–928, 1980; Reisenfeld et al., *J. Biol. Chem.* 257:421–425, 1982). Based on the differential sensitivity to inhibitors, the two catalytic sites appear to behave somewhat independently.

It was also determined that the N-deacetylase activity of the soluble enzyme was not stimulated by the addition of PAPS (FIG. 7C), in contrast with the findings of Riesenfeld et al. (*J. Biol. Chem.* 257:421–425, 1982) who reported that PAPS stimulated N-deacetylase activity in microsomal preparations from mast cells, and attributed this effect to a stimulatory effect of newly incorporated N-sulfate groups on the N-deacetylation reaction in heparin synthesis. In this respect, the HS-NdAC-NST is similar to the activity in CHO cells that directs heparan sulfate biosynthesis, although the inclusion of PAPS in in vitro assays of crude preparations of N-deacetylase from CHO cells lowers the $K_m$ for the polysaccharide substrate. Additionally, the N-deacetylase activity of the HS-NdAC-NST soluble enzyme was not increased by the addition of histone or Polybrene.

Heparan sulfate and heparin display the same type of modifications of their carbohydrate backbone (Kjellen and Lindahl, *Annu. Rev. Biochem.* 60:443–457, 1991); however, differences in sulfate content, clustering of sulfate within regions of the polymer, and iduronic acid content suggest that different mechanisms control their overall biosynthesis. At the cellular level, heparin is made only in connective tissue-type mast cells and is stored in intracellular granules, while heparan sulfate is synthesized by virtually all animal cells and is found on large extracellular and cell surface proteoglycans (Gallagher et al., *Biochem. J.* 236:313–325, 1986). At the molecular level, a number of studies employing microsomal preparations suggest a large part of the microheterogeneity found in both of these molecules is probably the result of incomplete processing by the enzymatic machinery (Kjellen and Lindahl, *Annu. Rev. Biochem.* 60:443–457, 1991). N-deacetylation and N-sulfation are hypothesized to be key steps in the biosynthesis of heparan sulfate and heparin in that C5-epimerization and O-sulfation occur only within or adjacent to N-sulfated domains (Bame et al., *J. Biol. Chem.* 266:10287–10293, 1991).

Although our observations show that the N-deacetylation and N-sulfation reactions require different conditions in vitro to obtain optimal activities, the two reactions are likely to be coupled in vivo. The availability of the nucleic acid sequence information for the full-length and soluble forms of the enzyme will now make it possible to dissect the mechanisms involved in the regulation of the modifications of heparan sulfate and heparin at the molecular level.

Expression of Polypeptides

Polypeptides according to the invention may be produced by expression from a recombinant nucleic acid having a sequence encoding part or all of a deacetylase/sulfotransferase of the invention, using any appropriate expression system: e.g., transformation of a suitable host cell (either prokaryotic or eukaryotic) with the recombinant nucleic acid in a suitable expression vehicle (e.g., pcDNAI). The precise host cell used is not critical to the invention; however, the following host cells are preferred: COS cells, CHO cells, and 293 cells (human kidney-derived fibroblasts). The method of transfection and the choice of expression vehicle will depend on the host system selected. Mammalian cell transfection methods are described, e.g., in Ausubel et al. (*Current Protocols in Molecular Biology*, John Wiley & Sons, New York, 1989); expression vehicles may be chosen from those discussed, e.g., in *Cloning Vectors: A Laboratory Manual* (P. H. Pouwels et al., 1985, Supp. 1987). Stably transfected cells are produced by integration of N-HSST DNA into the host cell chromosomes. For example, suitable DNAs are inserted into pcDNA, pcDNAI-Neo, or another suitable plasmid, and then cells are transfected with this plasmid with or without cotransfection with psV-2-Neo, or psV-2-DHFR by standard electroporation, calcium phosphate, and/or DEAE/Dextran techniques. Selection of transfected cells is performed using progressively increasing levels of G418 (Geneticin, GIBCO), and if necessary, methotrexate.

DNA sequences encoding the polypeptides of the invention can also be expressed in a prokaryotic host cell. DNA encoding a deacetylase/sulfotransferase of the invention or a fragment thereof is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. For example, *E. coli* may be transformed using derivatives of pBR322, a plasmid constructed by Bolivar et al. (Gene 2:95, 1977) using fragments derived from three naturally-occurring plasmids, two isolated from species of Salmonella, and one isolated from *E. coli*. pBR322 contains genes from ampicillin and tetracycline resistance, and thus provides multiple selectable markers which can be either retained or destroyed in constructing the desired expression vector. Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., *Nature* 198: 1056, 1977) and the tryptophan (Trp) promoter systems (Goeddel et al., Nucl. Acids Res. 8:4057, 1980) as well as the lambda-derived $P_L$ promoter and N-gene ribosome binding site (Simatake et al., Nature 292:128, 1981).

Soluble Polypeptides

The invention also includes soluble forms of the polypeptides of the invention. The predicted amino acid sequence of the rat N-heparan sulfate-N-deacetylase-N-sulfotransferase (SEQ ID NO.:1) indicates the presence of a membrane binding domain from amino acids 18 to 39. With this knowledge, one skilled in the art, using standard methods such as those described herein, could construct DNA clones in which the nucleotides encoding this region have been deleted. For example, a series of soluble forms of the enzyme can be constructed using PCR-based amplifications of the full-length cDNA with specific oligonucleotides which lack the membrane spanning region. The protein products produced by the resultant clones can then be affinity purified using antibody to the enzyme or by the methods described herein. Alternatively, oligonucleotides can be utilized to create fusion proteins that can be affinity purified based on the other component of the chimeric protein. For instance, a soluble form of the enzyme may be "fused" with Protein-A and purified by binding this chimera to IgG-Sepharose (see Sanchez-Lopez et al., *J. Biol. Chem.* 263:11892, 1988). A wide variety of systems for creating fusion proteins are available commercially.

Anti-Sulfotransferase Antibodies

The sulfotransferase polypeptides of the invention may be used to generate antibodies by any conventional method well known to those skilled in the art, including those which generate polyclonal antibodies and those which generate monoclonal antibodies. For example, the information given by the predicted amino acid sequence of the rat N-heparan sulfate-N-deacetylase-N-sulfotransferase (SEQ ID NO.:1) can be used to guide the selection of regions of the enzyme which would be likely to be involved in one or more of the functions of the enzyme. A short peptide representing the selected region may be synthesized (e.g., chemically or by recombinant DNA techniques) and used to immunize an animal (e.g., a rabbit or a mouse) to generate polyclonal or monoclonal antibodies.

Use

Using the methods described herein, overexpression of the nucleic acids of the invention may be used to isolate large quantities of polypeptides which are capable of efficiently catalyzing either the sulfation, deacetylation, or both the sulfation and deacetylation of various molecules including, but not limited to, heparin and heparan sulfate.

For example, the enzyme produced by DNA encoding the entire glycosaminoglycan specific deacetylase/sulfotransferase protein can be used to stimulate the efficient deacetylation and sulfation of purified or partially purified unsulfated glycosaminoglycans, to remove additional acetate groups, or to add additional sulfate groups to undersulfated glycosaminoglycans such as those prepared by previous methods. In addition, large quantities of the enzyme may be used to stimulate the deacetylation and/or sulfation of glycosaminoglycans at sites not usually deacetylated and/or sulfated under normal conditions thus producing glycosaminoglycans with novel structures and properties which can be characterized by standard methods.

In addition, polypeptide fragments produced by DNA encoding only part of the entire glycosaminoglycan specific deacetylase/sulfotransferase and which demonstrate altered specificities can be used to drive the deacetylation and/or sulfation of molecules which are not normally substrates for the intact enzyme, e.g., other proteoglycans and polysaccharides. For example, it is now known that at least one strain of E. coli, K5, contains a capsular polysaccharide which has the same structure as the non-sulfated precursor polysaccharide in heparin biosynthesis (Kushe et al., Biochem. J. 275:151, 1991).

Alternatively, expression of the nucleic acids of the invention can be used to produce polypeptides for in vivo deacetylation and/or sulfation of molecules. For example, the enzyme may be used for the biosynthesis of large quantities of efficiently sulfated heparin or heparan sulfate in bacterial cells, e.g, bacterial strains may be constructed which contain both the DNA encoding one or both of these proteoglycans and the DNA encoding the deacetylase/sulfotransferase of the invention. The heparin and heparan sulfate may then be isolated using standard methods.

The polypeptides and antibodies of the invention are useful for the treatment of disorders which may be characterized as being related to the interaction of sulfated proteoglycans, i.e., heparin and heparan sulfate, with other molecules. For example, it has been demonstrated that heparan sulfate and heparin play a critical role in the modulation of the mitogenic effects of heparin-binding growth factors in normal and neoplastic tissues (Yayon et al., Cell 64:841, 1991; Klagsbrun et al., Cell 67:229, 1991). In addition, heparan sulfate also serves as a cell surface receptor for herpes simplex virus (HSV) types 1 and 2, and thus, is required for viral absorption and infection (WuDunn et al., J. Virol. 63:52, 1989).

In one application, the polypeptides of the invention, or antibodies which have been determined (by the assays described herein) to stimulate native glycosaminoglycan specific sulfotransferase activity, deacetylase activity, or both sulfotransferase and deacetylase activity will be admixed with a pharmaceutically acceptable carrier substance, e.g., physiological saline, and administered to a mammal, e.g., a human, suffering from a disorder which is the result of a deficiency of efficiently sulfated heparin and heparan sulfate, e.g., blood-clotting disorders and certain neoplastic conditions. The particular mode of administration (e.g., intravenously, intramuscularly, orally, parenterally, or transdermally) will depend upon the condition being treated and the general status of the animal and will be apparent to those skilled in the art. The dosage of polypeptide or antibody will also vary, depending on such factors as the type and severity of the disease, but will generally be at a dosage sufficient to stimulate adequate sulfation of heparin and heparan sulfate. A typical dosage range would be 1 ng to 10 mg of the antibody or peptide per kg body weight per day. Treatment may be repeated as deemed necessary.

In another application, the antibodies of the invention which have been characterized, according to the methods described herein, as being capable of neutralizing one or both catalytic activities of a glycosaminoglycan specific deacetylase/sulfotransferase will be used to treat disorder in which the reduction of heparin and heparan sulfate levels are desirable, e.g., certain neoplastic conditions and viral infection. These antibodies will be formulated in a pharmaceutically acceptable carrier substance and administered by one of the modes described above at a dosage sufficient to inhibit the sulfation of heparin and heparan sulfate. A typical dosage range would be 1 ng to 10 mg of the antibody or peptide per kg body weight per day. Treatment may be repeated as deemed necessary.

The nucleic acids of the invention may also be used therapeutically. Oligonucleotides which are antisense to glycosaminoglycan specific deacetylase/sulfotransferase mRNA (or nucleic acid constructs which express RNA that is antisense to glycosaminoglycan specific deacetylase/sulfotransferase mRNA) may be utilized as an anticancer therapy, e.g., in those cases characterized by amplified levels of receptor binding of heparin-binding growth factors. The method would involve introduction of the antisense oligonucleotide into the tumor cells in vivo. The antisense DNA hybridizes with endogenous glycosaminoglycan specific deacetylase/sulfotransferase mRNA, interfering with translation of the protein, thereby reducing production of the enzyme in such cells, and accordingly, the level of heparin and heparan sulfate. Methods for antisense design and introduction into host cells are described, for example in Weinberg et al., U.S. Pat. No. 4,740,463, herein incorporated by reference.

Nucleic acids of the invention which encode a polypeptide with glycosaminoglycan specific sulfotransferase activity, deacetylase activity, or both sulfotransferase and deacetylase activity may also be linked to a selected tissue-specific promoter and/or enhancer and the resultant hybrid gene introduced, by standard methods (e.g., as described by Leder et al, U.S. Pat. No. 4,736,866, herein incorporated by reference), into an animal embryo at an early developmental stage (e.g., the fertilized oocyte stage), to produce a transgenic animal which expresses elevated levels of the desired activity in selected tissues (e.g., neuroectodermal, endothelial, angiogenic, and others). The form of DNA utilized can be one which encodes an enzyme with a sulfotransferase and/or deacetylase activity similar to the animal species used, or it can encode the homolog of a different species (e.g., human). Such an animal would be useful as an in vivo model for neoplastic disease in the selected tissues. In addition, cells derived from such a transgenic animal may be used to establish an immortal cell line that retains at least some of its differentiated characteristics while proliferating indefinitely in vitro.

Other Embodiments

Other embodiments are within the following claims. For example, the invention includes any protein which is substantially homologous to rat N-heparan sulfate-N-deacetylase/N-sulfotransferase (FIGS. 3A to 3F, SEQ ID NO:1) as well as other naturally occurring deacetylase/sulfotransferases. Also included are: allelic variations; natural mutants; induced mutants; chimeric polypeptides that include a polypeptide with sulfotransferase and/or deacetylase activity; proteins encoded by DNA that hybridizes under high or low stringency conditions (e.g., see Current Protocols in Molecular Biology, John Wiley & Sons, New York, 1989, 6.3.1—6.3.1, hereby incorporated by reference) to a naturally occurring nucleic acid; and polypeptides or proteins specifically bound by antisera to N-heparan sulfate-N-deacetylase-N-sulfotransferase, especially by antisera to either the sulfotransferase or deacetylase active sites of the enzyme.

The invention also includes biologically active polypeptide fragments or analogs of the recombinantly produced deacetylase/sulfotransferase of the invention. By "biologically active" is meant possessing any in vivo or in vitro activity which is characteristic of the deacetylase/sulfotransferase of the invention. A polypeptide fragment possessing at least 10%, preferably 40%, or most preferably 90% of the activity of the N-heparan sulfate-N-deacetylase-N-sulfotransferase (shown in FIGS. 3A to 3F; SEQ ID NO:1), in any in vivo or in vitro sulfotransferase and/or deacetylase assays is considered biologically active and useful in the invention. As used herein, the term "fragment", as applied to a polypeptide, will ordinarily be at least about 20 contiguous amino acids, preferably at least 40 contiguous amino acids, and most preferably at least 60 to 80 contiguous amino acids in length. Polypeptide fragments can be generated by methods known to those skilled in the art, and the ability of a candidate fragment to exhibit a biological activity of a sulfotransferase can be assessed by methods known to those skilled in the art.

Preferred analogs of the invention include N-heparan sulfate-N-deacetylase-N-sulfotransferases (or biologically active fragments thereof) whose sequences differ from the naturally occurring N-heparan sulfate-N-deacetylase-N-sulfotransferase by amino acid sequence differences or by modifications that do not affect sequence, or by both. Analogs of the invention will generally exhibit at least 70%, preferably 80%, more preferably 90%, and most preferably at least 95% or even 99%, homology with all or part of a naturally occurring N-heparan sulfate-N-deacetylase-N-sulfotransferase. The length of comparison sequences will generally be at least about 20 amino acid residues, and preferably more than 40 amino acid residues. Differences in amino acid sequence may be by conservative amino acid substitutions, for example substitution of one amino acid for another of the same class (e.g., valine for glycine, arginine for lysine, etc.) or by one or more non-conservative amino acid substitutions, deletions, or insertions which do not destroy the analog's biological activity as measured by in vivo or in vitro sulfotransferase and/or deacetylase assays. Modifications include in vivo or in vitro chemical derivatization of polypeptides, e.g, acetylation, or carboxylation. Also included are modifications of glycosylation, e.g., those made by modifying the glycosylation patterns of a polypeptide during its synthesis and processing or in further processing steps, e.g., by exposing the polypeptide to glycosylating affecting enzymes from cells that normally provide such processing, e.g., mammalian glycosylation enzymes. Also embraced are versions of the same primary amino acid sequence that have phosphorylated amino acid residues, e.g., phosphotyrosine, phosphoserine, or phosphothreonine; and analogs that include residues other than naturally occurring L-amino acids, e.g., D-amino acids or non-naturally occurring or synthetic amino acids, e.g., $\beta$ or $\gamma$ amino acids. Preferred analogs also include N-heparan sulfate-N-deacetylase-N-sulfotransferases (or biologically active fragments thereof) which are modified for the purpose of increasing peptide stability, e.g., one or more desaturated peptide bonds, or non-peptide bonds. Alternatively, increased stability may be conferred by cyclizing the peptide molecule.

What is claimed is:

1. Isolated DNA consisting of a DNA sequence encoding a glycosaminoglycan-specific N-deacetylase-N-sulfotransferase having the amino acid sequence shown in FIG. 3 (SEQ ID NO:1) or a soluble fragment of said N-deacetylase-N-sulfotransferase.

2. A vector containing the isolated DNA of claim 1.

3. A recombinant cell containing the isolated DNA of claim 1.

4. The cell of claim 3 wherein said cell is capable of expressing from said DNA a polypeptide which catalyzes the N-sulfation and N-deacetylation of heparan sulfate or heparin.

5. An essentially homogenous population of recombinant cells, each of which comprises the isolated DNA of claim 1.

6. A method for manufacture of a polypeptide capable of catalyzing the N-deacetylation and N-sulfation of heparan sulfate or heparin, said method comprising:

providing a recombinant cell comprising the isolated DNA of claim 1;

culturing said cell in a medium under conditions permitting expression of said polypeptide; and purifying said polypeptide from said cell or said medium.

7. A single-stranded DNA comprising a portion of the sense or antisense strand of the DNA of claim 1, wherein said portion is at least 18 nucleotides long.

8. The single-stranded DNA of claim 7, wherein said single-stranded DNA is antisense.

9. A method for identifying a DNA sequence encoding a glycosaminoglycan-specific N-deacetylase-N-sulfotransferase of a mammal, said method comprising:

providing a genomic or cDNA library from said mammal;

contacting said library with the single-stranded DNA of claim 7, under conditions permitting hybridization between said single-stranded DNA and any complementary DNA sequences in said library; and identifying a clone from said library which hybridizes to said single-stranded DNA, said hybridization indicating the presence in said clone of a DNA sequence encoding all or a portion of a glycosaminoglycan-specific N-deacetylase-N-sulfotransferase from said mammal having the amino acid sequence shown in FIG. 3 (SEQ ID NO:1).

10. The isolated DNA of claim 1, wherein said DNA encodes the Golgi-lumenal portion of said glycosaminoglycan-specific N-deacetylase-N-sulfotransferase.

11. The cell of claim 4, wherein said DNA encodes the Golgi-lumenal portion of a glycosaminoglycan-specific N-deacetylase-N-sulfotransferase.

12. The cell of claim 4, wherein said DNA encodes amino acids 42 to 882 of the amino acid sequence shown in FIG. 3 (SEQ ID NO:1).

13. A method for manufacture of a soluble polypeptide capable of catalyzing the N-deacetylation and N-sulfation of heparan sulfate or heparin, said method comprising:

providing a recombinant cell comprising the isolated DNA of claim 10;

culturing said cell in a medium under conditions permitting expression of said polypeptide; and purifying said polypeptide from said cell or said medium.

14. Isolated DNA encoding a soluble fusion polypeptide which catalyzes the N-sulfation and N-deacetylation of heparan sulfate or heparin, said fusion polypeptide consisting of the golgi-lumenal portion of the glycosaminoglycan-specific N-deacetylase-N-sulfotransferase of claim 1 fused to a second protein.

15. The isolated DNA of claim 14, wherein said second protein is the IgG binding portion of Protein A.

16. A method for manufacture of a soluble fusion polypeptide which catalyzes the N-sulfation and N-deacetylation of heparan sulfate or heparin, said method comprising, providing a recombinant cell comprising the isolated DNA of claim 15;

culturing said cell in a medium under conditions permitting expression of said fusion polypeptide; and purifying said fusion polypeptide from said medium by affinity chromatography using IgG agarose.

17. The isolated DNA of claim 1, wherein said DNA sequence encodes amino acids 42 to 882 of the amino acid sequence shown in FIG. 3 (SEQ ID NO:1).

* * * * *

UNITED STATES PATENT AND TRADEMARK OFFICE
CERTIFICATE OF CORRECTION

PATENT NO. : 5,541,095

DATED : July 30, 1996

INVENTOR(S) : Hirschberg et al.

It is certified that error appears in the above-identified patent and that said Letters Patent is hereby corrected as shown below:

On the title page: Item [56]

In "Other Publications"

In right column, on line 6, after "Wight et al.", insert -- eds. --;

Col. 5, line 25, after "are", delete "is";

Col. 11, Table II, underline "PLATE 2";

Col. 11, Table II, before "nd", insert -- * --;

In the Claims

Claim 1, col. 33, line 27, after "fragment", insert -- comprising the Golgi-lumenal portion --;

Claim 9, col. 33, line 53, after "specific", delete the extra space.

Signed and Sealed this

Sixth Day of January, 1998

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
( A ) LENGTH: 4052
( B ) TYPE: nucleic acid
( C ) STRANDEDNESS: single
( D ) TOPOLOGY: linear ( x i ) SEQUENCE DESCRIPTION: SEQ ID NO: 1:

```
GAATTCCAAG  ACAGAATATC  AGTCCTCCCT  CCGTTTCCCA  GGTCAGCTCC  CTAGCCTTTA      60

CCCTGTGGGC  CCAACGTGAA  GAGCGTGAAG  AGCGCGGCAT  GCAGCACCCC  CTGGCTGGCC     120

CGGTGTCTTT  TGACCTGCTG  TTGACTGCTC  CCAGGAGGCC  CTGACGCCCT  GGGGCACTTT     180

TGCTCTGCAC  AGGACCACGT  TGGGGTTTGC  CATGGTGACA  TAAAGGGGTG  TAGAGGAAGG     240

AAGGAGCAAG  ACCAGCCTGT  AGACTGTGCC  CCTGGCTGGG  CGAAAGGGCC  AGGGGCCCGG     300

AGCCTTCTCT  CCACTGCCCT  CTGAACGTCT  CACTTCCTAA  GTCTCTGCAT  TTCTCAGTCA     360

GTGGACAACT  TTTGGAACTC  CTGTGTGAGG  ACTTCGGGGG  ACCAGGCCAG  GCTGGGCCTC     420

TGCTGGTTGA  GATCTCGGGG  GCCAGA                                             446
```

ATG CCT GCC CTG GCG TGC CTC CGG AGG CTG TGT CGG CAC CTG TCC CCA   494
Met Pro Ala Leu Ala Cys Leu Arg Arg Leu Cys Arg His Leu Ser Pro
 1               5                  10                  15

CAG GCT GTC CTG TTC CTG CTG TTT GTC TTC TGC CTG TTC AGC GTG TTT   542
Gln Ala Val Leu Phe Leu Leu Phe Val Phe Cys Leu Phe Ser Val Phe
            20                  25                  30

| | | | | | | | | | | | | | | | | |
|---|---|---|---|---|---|---|---|---|---|---|---|---|---|---|---|---|
| GTC | TCG | GCC | TAC | TAC | CTA | TAT | GGT | TGG | AAC | CGG | GGC | CTC | GAG | CCC | TCG | 590 |
| Val | Ser | Ala | Tyr | Tyr | Leu | Tyr | Gly | Trp | Asn | Arg | Gly | Leu | Glu | Pro | Ser | |
| | | 35 | | | | 40 | | | | | 45 | | | | | |
| GCA | GAT | GCT | TCT | GAG | TCC | GAC | TGC | GGG | GAC | CCA | CCA | CCT | GTC | GCC | CCT | 638 |
| Ala | Asp | Ala | Ser | Glu | Ser | Asp | Cys | Gly | Asp | Pro | Pro | Pro | Val | Ala | Pro | |
| | 50 | | | | 55 | | | | | 60 | | | | | | |
| AGC | CGT | CTC | CTG | CCA | ATC | AAG | CCT | GTG | CAG | GCG | GTC | GCC | CCT | TCT | CGA | 686 |
| Ser | Arg | Leu | Leu | Pro | Ile | Lys | Pro | Val | Gln | Ala | Val | Ala | Pro | Ser | Arg | |
| 65 | | | | | 70 | | | | | 75 | | | | | 80 | |
| ACA | GAC | CCG | CTG | GTG | CTG | GTA | TTT | GTG | GAG | AGC | CTC | TAT | TCA | CAG | CTG | 734 |
| Thr | Asp | Pro | Leu | Val | Leu | Val | Phe | Val | Glu | Ser | Leu | Tyr | Ser | Gln | Leu | |
| | | | | 85 | | | | | 90 | | | | | 95 | | |
| GGC | CAG | GAG | GTG | GTG | GCC | ATC | CTG | GAA | TCC | AGT | CGC | TTC | AAG | TAC | CGA | 782 |
| Gly | Gln | Glu | Val | Val | Ala | Ile | Leu | Glu | Ser | Ser | Arg | Phe | Lys | Tyr | Arg | |
| | | | 100 | | | | | 105 | | | | | 110 | | | |
| ACA | GAA | ATT | GCA | CCG | GGG | AAG | GGG | GAC | ATG | CCC | ACA | CTC | ACA | GAC | AAG | 830 |
| Thr | Glu | Ile | Ala | Pro | Gly | Lys | Gly | Asp | Met | Pro | Thr | Leu | Thr | Asp | Lys | |
| | | 115 | | | | | 120 | | | | | 125 | | | | |
| GGC | CGA | GGC | CGC | TTC | GCC | CTC | ATC | ATC | TAT | GAG | AAC | ATC | CTC | AAG | TAT | 878 |
| Gly | Arg | Gly | Arg | Phe | Ala | Leu | Ile | Ile | Tyr | Glu | Asn | Ile | Leu | Lys | Tyr | |
| | 130 | | | | | 135 | | | | | 140 | | | | | |
| GTC | AAC | CTG | GAT | GCC | TGG | AAC | CGG | GAG | CTG | CTG | GAC | AAG | TAC | TGT | GTG | 926 |
| Val | Asn | Leu | Asp | Ala | Trp | Asn | Arg | Glu | Leu | Leu | Asp | Lys | Tyr | Cys | Val | |
| 145 | | | | | 150 | | | | | 155 | | | | | 160 | |
| GCC | TAC | GGC | GTG | GGC | ATC | ATT | GGC | TTC | TTC | AAG | GCC | AAT | GAG | AAC | AGC | 974 |
| Ala | Tyr | Gly | Val | Gly | Ile | Ile | Gly | Phe | Phe | Lys | Ala | Asn | Glu | Asn | Ser | |
| | | | | 165 | | | | | 170 | | | | | 175 | | |
| CTG | CTG | AGT | GCA | CAG | CTC | AAA | GGC | TTC | CCT | CTT | TTC | CTG | CAT | TCG | AAC | 1022 |
| Leu | Leu | Ser | Ala | Gln | Leu | Lys | Gly | Phe | Pro | Leu | Phe | Leu | His | Ser | Asn | |
| | | | 180 | | | | | 185 | | | | | 190 | | | |
| CTG | GGC | TTG | AAA | GAC | TGC | AGC | ATC | AAC | CCC | AAG | TCC | CCA | CTG | CTG | TAC | 1070 |
| Leu | Gly | Leu | Lys | Asp | Cys | Ser | Ile | Asn | Pro | Lys | Ser | Pro | Leu | Leu | Tyr | |
| | | 195 | | | | | 200 | | | | | 205 | | | | |
| GTG | ACA | CGG | CCC | AGT | GAG | GTA | GAG | AAA | GGT | GTG | CTG | CCC | GGA | GAG | GAC | 1118 |
| Val | Thr | Arg | Pro | Ser | Glu | Val | Glu | Lys | Gly | Val | Leu | Pro | Gly | Glu | Asp | |
| | 210 | | | | | 215 | | | | | 220 | | | | | |
| TGG | ACG | GTG | TTC | CAG | TCT | AAC | CAC | TCT | ACC | TAT | GAG | CCA | GTG | CTG | CTG | 1166 |
| Trp | Thr | Val | Phe | Gln | Ser | Asn | His | Ser | Thr | Tyr | Glu | Pro | Val | Leu | Leu | |
| 225 | | | | | 230 | | | | | 235 | | | | | 240 | |
| GCC | AAG | ACG | CGC | TCC | TCT | GAG | TCC | ATC | CCA | CAC | CTG | GGC | GCA | GAT | GCC | 1214 |
| Ala | Lys | Thr | Arg | Ser | Ser | Glu | Ser | Ile | Pro | His | Leu | Gly | Ala | Asp | Ala | |
| | | | | 245 | | | | | 250 | | | | | 255 | | |
| GGC | CTG | CAT | GCT | GCC | CTG | CAC | GCT | ACT | GTG | GTC | CAG | GAC | CTG | GGC | CTC | 1262 |
| Gly | Leu | His | Ala | Ala | Leu | His | Ala | Thr | Val | Val | Gln | Asp | Leu | Gly | Leu | |
| | | | 260 | | | | | 265 | | | | | 270 | | | |
| CAT | GAC | GGC | ATT | CAG | CGT | GTG | CTG | TTT | GGC | AAC | AAC | CTC | AAC | TTT | TGG | 1310 |
| His | Asp | Gly | Ile | Gln | Arg | Val | Leu | Phe | Gly | Asn | Asn | Leu | Asn | Phe | Trp | |
| | | 275 | | | | | 280 | | | | | 285 | | | | |
| CTG | CAT | AAG | CTC | GTC | TTC | GTG | GAC | GCT | GTG | GCC | TTC | CTC | ACA | GGG | AAG | 1358 |
| Leu | His | Lys | Leu | Val | Phe | Val | Asp | Ala | Val | Ala | Phe | Leu | Thr | Gly | Lys | |
| | | 290 | | | | | 295 | | | | | 300 | | | | |
| CGC | CTC | TCA | CTG | CCT | TTG | GAC | CGA | TAC | ATC | CTG | GTG | GAC | ATT | GAT | GAC | 1406 |
| Arg | Leu | Ser | Leu | Pro | Leu | Asp | Arg | Tyr | Ile | Leu | Val | Asp | Ile | Asp | Asp | |
| 305 | | | | | 310 | | | | | 315 | | | | | 320 | |
| ATT | TTT | GTA | GGC | AAG | GAG | GGC | ACA | CGC | ATG | AAG | GTG | GAG | GAT | GTG | AAG | 1454 |
| Ile | Phe | Val | Gly | Lys | Glu | Gly | Thr | Arg | Met | Lys | Val | Glu | Asp | Val | Lys | |
| | | | | 325 | | | | | 330 | | | | | 335 | | |
| GCC | CTG | TTT | GAT | ACA | CAG | AAT | GAA | CTT | CGT | ACA | CAT | ATC | CCA | AAC | TTC | 1502 |
| Ala | Leu | Phe | Asp | Thr | Gln | Asn | Glu | Leu | Arg | Thr | His | Ile | Pro | Asn | Phe | |
| | | | 340 | | | | | 345 | | | | | 350 | | | |

| | | | | | | | | | | | | | | | | |
|---|---|---|---|---|---|---|---|---|---|---|---|---|---|---|---|---|
| ACC | TTC | AAC | CTG | GGC | TAC | TCA | GGG | AAA | TTC | TTC | CAC | ACA | GGT | ACC | GAT | 1550 |
| Thr | Phe | Asn | Leu | Gly | Tyr | Ser | Gly | Lys | Phe | Phe | His | Thr | Gly | Thr | Asp | |
| | | 355 | | | | | 360 | | | | | 365 | | | | |
| GCT | GAG | GAT | GCT | GGG | GAC | GAC | CTG | CTG | CTG | TCC | TAT | GTG | AAA | GAG | TTC | 1598 |
| Ala | Glu | Asp | Ala | Gly | Asp | Asp | Leu | Leu | Leu | Ser | Tyr | Val | Lys | Glu | Phe | |
| | 370 | | | | | 375 | | | | | 380 | | | | | |
| TGG | TGG | TTC | CCC | CAC | ATG | TGG | AGC | CAT | ATG | CAA | CCC | CAC | CTC | TTC | CAC | 1646 |
| Trp | Trp | Phe | Pro | His | Met | Trp | Ser | His | Met | Gln | Pro | His | Leu | Phe | His | |
| 385 | | | | | 390 | | | | 395 | | | | | | 400 | |
| AAC | CAG | TCT | GTG | CTG | GCT | GAG | CAG | ATG | GCC | CTG | AAC | AAG | AAG | TTC | GCT | 1694 |
| Asn | Gln | Ser | Val | Leu | Ala | Glu | Gln | Met | Ala | Leu | Asn | Lys | Lys | Phe | Ala | |
| | | | | 405 | | | | | 410 | | | | | 415 | | |
| GTC | GAG | CAC | CCC | ATT | GGG | ACA | GAT | ATG | GGG | TAT | GCA | GTG | GCA | CCC | CAC | 1742 |
| Val | Glu | His | Pro | Ile | Gly | Thr | Asp | Met | Gly | Tyr | Ala | Val | Ala | Pro | His | |
| | | | 420 | | | | | 425 | | | | | 430 | | | |
| CAC | TCT | GGT | GTG | TAC | CCT | GTG | CAT | GTG | CAG | CTG | TAT | GAG | GCC | TGG | AAG | 1790 |
| His | Ser | Gly | Val | Tyr | Pro | Val | His | Val | Gln | Leu | Tyr | Glu | Ala | Trp | Lys | |
| | | 435 | | | | | 440 | | | | | 445 | | | | |
| CAA | GTG | TGG | AAC | ATC | CGT | GTG | ACC | AGC | ACA | GAG | GAG | TAC | CCG | CAT | CTG | 1838 |
| Gln | Val | Trp | Asn | Ile | Arg | Val | Thr | Ser | Thr | Glu | Glu | Tyr | Pro | His | Leu | |
| | 450 | | | | | 455 | | | | | 460 | | | | | |
| AAG | CCT | GCC | CGT | TAC | CGC | CGT | GGC | TTC | ATC | CAC | AAT | GGC | ATC | ATG | GTC | 1886 |
| Lys | Pro | Ala | Arg | Tyr | Arg | Arg | Gly | Phe | Ile | His | Asn | Gly | Ile | Met | Val | |
| 465 | | | | 470 | | | | | 475 | | | | | | 480 | |
| CTC | CCT | CGG | CAG | ACC | TGT | GGT | CTC | TTT | ACA | CAC | ACC | ATC | TTC | TAC | AAC | 1934 |
| Leu | Pro | Arg | Gln | Thr | Cys | Gly | Leu | Phe | Thr | His | Thr | Ile | Phe | Tyr | Asn | |
| | | | | 485 | | | | | 490 | | | | | 495 | | |
| GAG | TAC | CCT | GGA | GGC | TCC | AGT | GAG | CTG | GAC | AAG | ATC | ATC | AAT | GGG | GGC | 1982 |
| Glu | Tyr | Pro | Gly | Gly | Ser | Ser | Glu | Leu | Asp | Lys | Ile | Ile | Asn | Gly | Gly | |
| | | | 500 | | | | | 505 | | | | | 510 | | | |
| GAG | CTC | TTT | CTT | ACT | GTG | CTC | CTC | AAT | CCT | ATC | AGC | GTC | TTC | ATG | ACA | 2030 |
| Glu | Leu | Phe | Leu | Thr | Val | Leu | Leu | Asn | Pro | Ile | Ser | Val | Phe | Met | Thr | |
| | | 515 | | | | | 520 | | | | | 525 | | | | |
| CAC | TTA | TCC | AAC | TAT | GGA | AAT | GAC | CGC | CTG | GGA | CTG | TAC | ACC | TTC | AAG | 2078 |
| His | Leu | Ser | Asn | Tyr | Gly | Asn | Asp | Arg | Leu | Gly | Leu | Tyr | Thr | Phe | Lys | |
| | | 530 | | | | | 535 | | | | | 540 | | | | |
| CAC | CTG | GTG | CGC | TTC | CTG | CAC | TCC | TGG | ACC | AAC | CTG | AGG | CTG | CAG | ACG | 2126 |
| His | Leu | Val | Arg | Phe | Leu | His | Ser | Trp | Thr | Asn | Leu | Arg | Leu | Gln | Thr | |
| 545 | | | | | 550 | | | | | 555 | | | | | 560 | |
| CTG | CCC | CCT | GTG | CAG | CTG | GCC | CAG | AAG | TAC | TTC | CAG | ATC | TTT | TCT | GAG | 2174 |
| Leu | Pro | Pro | Val | Gln | Leu | Ala | Gln | Lys | Tyr | Phe | Gln | Ile | Phe | Ser | Glu | |
| | | | | 565 | | | | | 570 | | | | | 575 | | |
| GAG | AAG | GAC | CCA | CTT | TGG | CAG | GAT | CCC | TGT | GAG | GAC | AAA | CGC | CAC | AAA | 2222 |
| Glu | Lys | Asp | Pro | Leu | Trp | Gln | Asp | Pro | Cys | Glu | Asp | Lys | Arg | His | Lys | |
| | | | 580 | | | | | 585 | | | | | 590 | | | |
| GAC | ATC | TGG | TCT | AAG | GAG | AAG | ACA | TGT | GAT | CGC | TTC | CCA | AAG | CTG | CTC | 2270 |
| Asp | Ile | Trp | Ser | Lys | Glu | Lys | Thr | Cys | Asp | Arg | Phe | Pro | Lys | Leu | Leu | |
| | | 595 | | | | | 600 | | | | | 605 | | | | |
| ATC | ATT | GGC | CCC | CAG | AAA | ACA | GGC | ACC | ACA | GCC | CTC | TAC | CTG | TTC | CTG | 2318 |
| Ile | Ile | Gly | Pro | Gln | Lys | Thr | Gly | Thr | Thr | Ala | Leu | Tyr | Leu | Phe | Leu | |
| | 610 | | | | | 615 | | | | | 620 | | | | | |
| GGC | ATG | CAC | CCC | GAC | CTC | AGC | AGC | AAC | TAC | CCC | AGC | TCC | GAG | ACC | TTT | 2366 |
| Gly | Met | His | Pro | Asp | Leu | Ser | Ser | Asn | Tyr | Pro | Ser | Ser | Glu | Thr | Phe | |
| 625 | | | | | 630 | | | | | 635 | | | | | 640 | |
| GAG | GAG | ATC | CAG | TTT | TTT | AAT | GGC | CAC | AAC | TAT | CAC | AAA | GGC | ATC | GAC | 2414 |
| Glu | Glu | Ile | Gln | Phe | Phe | Asn | Gly | His | Asn | Tyr | His | Lys | Gly | Ile | Asp | |
| | | | | 645 | | | | | 650 | | | | | 655 | | |
| TGG | TAC | ATG | GAA | TTC | TTC | CCT | ATT | CCC | TCC | AAC | ACC | ACC | TCT | GAC | TTC | 2462 |
| Trp | Tyr | Met | Glu | Phe | Phe | Pro | Ile | Pro | Ser | Asn | Thr | Thr | Ser | Asp | Phe | |
| | | | | 660 | | | | | 665 | | | | | 670 | | |

| | | | | | | | | | | | | | | | | |
|---|---|---|---|---|---|---|---|---|---|---|---|---|---|---|---|---|
| TAC | TTT | GAA | AAA | AGT | GCC | AAC | TAC | TTT | GAT | TCA | GAA | GTG | GCA | CCA | CGG | 2510 |
| Tyr | Phe | Glu 675 | Lys | Ser | Ala | Asn | Tyr 680 | Phe | Asp | Ser | Glu | Val 685 | Ala | Pro | Arg | |
| CGA | GCA | GCT | GCC | CTA | TTG | CCC | AAG | GCC | AAG | GTT | CTC | ACC | ATC | CTC | ATC | 2558 |
| Arg | Ala 690 | Ala | Ala | Leu | Leu | Pro 695 | Lys | Ala | Lys | Val | Leu 700 | Thr | Ile | Leu | Ile | |
| AAT | CCA | GCC | GAC | CGG | GCT | TAC | TCC | TGG | TAC | CAG | CAC | CAG | CGG | GCC | CAT | 2606 |
| Asn 705 | Pro | Ala | Asp | Arg | Ala 710 | Tyr | Ser | Trp | Tyr | Gln 715 | His | Gln | Arg | Ala | His 720 | |
| GAT | GAC | CCG | GTG | GCC | CTA | AAG | TAC | ACC | TTC | CAT | GAG | GTG | ATC | ACA | GCT | 2654 |
| Asp | Asp | Pro | Val | Ala 725 | Leu | Lys | Tyr | Thr | Phe 730 | His | Glu | Val | Ile | Thr 735 | Ala | |
| GGC | CCT | GAC | GCA | TCC | TCA | AAG | CTG | CGT | GCC | CTC | CAG | AAC | CGA | TGC | CTG | 2702 |
| Gly | Pro | Asp | Ala 740 | Ser | Ser | Lys | Leu | Arg 745 | Ala | Leu | Gln | Asn | Arg 750 | Cys | Leu | |
| GTC | CCC | GGC | TGG | TAT | GCC | ACT | CAT | ATT | GAA | CGC | TGG | CTC | AGC | GCC | TTT | 2750 |
| Val | Pro | Gly 755 | Trp | Tyr | Ala | Thr | His 760 | Ile | Glu | Arg | Trp | Leu 765 | Ser | Ala | Phe | |
| CAT | GCC | AAC | CAG | ATC | CTG | GTC | TTG | GAT | GGC | AAA | CTG | CTG | CGA | ACA | GAA | 2798 |
| His | Ala | Asn 770 | Gln | Ile | Leu | Val 775 | Leu | Asp | Gly | Lys | Leu 780 | Leu | Arg | Thr | Glu | |
| CCT | GCC | AAA | GTG | ATG | GAC | ACA | GTG | CAG | AAA | TTC | CTC | GGG | GTG | ACC | AGC | 2846 |
| Pro 785 | Ala | Lys | Val | Met | Asp 790 | Thr | Val | Gln | Lys | Phe 795 | Leu | Gly | Val | Thr | Ser 800 | |
| ACG | GTT | GAC | TAC | CAT | AAA | ACC | TTG | GCG | TTT | GAC | CCA | AAG | AAA | GGA | TTT | 2894 |
| Thr | Val | Asp | Tyr | His 805 | Lys | Thr | Leu | Ala | Phe 810 | Asp | Pro | Lys | Lys | Gly 815 | Phe | |
| TGG | TGC | CAG | CTG | CTC | GAA | GGA | GGA | AAA | ACC | AAG | TGT | CTG | GGA | AAA | AGC | 2942 |
| Trp | Cys | Gln | Leu 820 | Leu | Glu | Gly | Gly | Lys 825 | Thr | Lys | Cys | Leu | Gly 830 | Lys | Ser | |
| AAG | GGA | CGG | AAA | TAT | CCA | GAG | ATG | GAC | CTG | GAT | TCC | CGA | GCC | TTC | CTA | 2990 |
| Lys | Gly | Arg 835 | Lys | Tyr | Pro | Glu | Met 840 | Asp | Leu | Asp | Ser | Arg 845 | Ala | Phe | Leu | |
| AAG | GAT | TAC | TAC | CGG | GAC | CAC | AAC | ATT | GAG | CTC | TCT | AAG | CTG | CTG | TAT | 3038 |
| Lys | Asp | Tyr 850 | Tyr | Arg | Asp | His | Asn 855 | Ile | Glu | Leu | Ser | Lys 860 | Leu | Leu | Tyr | |
| AAG | ATG | GGC | CAG | ACA | CTG | CCC | ACC | TGG | CTG | CGG | GAA | GAC | CTC | CAG | AAC | 3086 |
| Lys 865 | Met | Gly | Gln | Thr | Leu 870 | Pro | Thr | Trp | Leu | Arg 875 | Glu | Asp | Leu | Gln | Asn 880 | |
| ACC | AGG | | | | | | | | | | | | | | | 3092 |
| Thr | Arg | | | | | | | | | | | | | | | |

```
TAGCCTTGGC CACCACAGCC AGCCAGAACG CTTGTGTTAG CAGGGATGTC CTGCCTCACA    3152
CTGAGCCAGA CTGACCTGCC TCGAAGGATG CTGGCCCCAG CCAGCCAGGA GCAACGAGCA    3212
ATACCCTGCT AAGGCCCACC AGAGCCGGAA GCCCAGGCAG GTCTGCCCTC TGTGGGACCA    3272
GAGGTCCATT CCGTTCCTTC GCAGCCTCCC TGCCTGGGGA GAGCACAAGC GCCTCAGAGC    3332
ATCCACTGCT GGATGTGTGG CTGTGGGATT CCTGTTGGTG AAGGTCATT  TCCTGGTAGG    3392
AGGAGTCCTG GAGACTCTCT CCTGTCCCTC ACTGTGTTCG GCCAGTCCTG CCCTGTTCTG    3452
TGTCATACCA CCCCTGCTCC AGCAGGATGT CCCCTCAGTA TTAGCTGTCA TATTTCTCTG    3512
TCCTCCAGAC AGTAAGGGAG AGGAGCGCAG CTGGGCCTCT CGCCCAACTA GAGAGAAAGA    3572
CTGGGCATGT CCCTGAGGGT TTGAGCCAGG CCCCGCCAGG GTTAGGTAG  GCACCCAGAT    3632
GCACTCATAG ATTGAATGTG AGGGTGGCCA TCTTGAGAGG ACATACGACT CAGTATTTGG    3692
GTTATTAGTA TCAATCTCAT CTCCCCTTTG GGGAAAGAC  TCTCTGGTCC CCTATTGTAT    3752
CCACCTAGTG CTCATGGTCT CTTGTTGGCC CTGGGCCACT GCCCTGCCAC TGGGCCAGA    3812
GACATGGGCC TTGGCCCTGT CCTGTTCACC TGGATGTGAC CTGTGGTGTT TCCTGTGGTA    3872
```

AAGGCTGAGG CGAGTCAGGA GTCTGCCAGT GTTCATACTC CCATGTACAT ATACACTGTC 3932

TCCCAGCCAC CGCCTCGGCC CGGCAGGCAA GCAGAGTCAG CAGCACTGCT CTCTACTGCT 3992

TTGCCTGGCA ACCTGTGGCT GAGGGTCCCC AGAGACCCCC CCAACCTCCC AAATACTAAG 4052

( 2 ) INFORMATION FOR SEQ ID NO: 2:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i x ) FEATURE:
        ( D ) OTHER INFORMATION: N is inosine ( x i ) SEQUENCE DESCRIPTION: SEQ ID NO: 2:

GCNAAYTAYT TYGAYWSNGA RGT 23

( 2 ) INFORMATION FOR SEQ ID NO: 3:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i x ) FEATURE:
        ( D ) OTHER INFORMATION: N is inosine ( x i ) SEQUENCE DESCRIPTION: SEQ ID NO: 3:

CTRGTRTTRT ANCTYRANWS NTTY 24

( 2 ) INFORMATION FOR SEQ ID NO: 4:

( i ) SEQUENCE CHARACTERISTICS:
        ( A ) LENGTH: 23
        ( B ) TYPE: nucleic acid
        ( C ) STRANDEDNESS: single
        ( D ) TOPOLOGY: linear ( i x ) FEATURE:
        ( D ) OTHER INFORMATION: N is inosine ( x i ) SEQUENCE DESCRIPTION: SEQ ID NO: 4:

GCNCAYGAYG AYCCNGTNGT NYT 23

( 2 ) INFORMATION FOR SEQ ID NO: 5:

( i ) SEQUENCE CHARACTERISTICS:
        ( A ) LENGTH: 24
        ( B ) TYPE: nucleic acid
        ( C ) STRANDEDNESS: single
        ( D ) TOPOLOGY: linear ( i x ) FEATURE:
        ( D ) OTHER INFORMATION: N is inosine ( x i ) SEQUENCE DESCRIPTION: SEQ ID NO: 5:

GTRCTRCTRG GNCANCGNRA NTTY 24

( 2 ) INFORMATION FOR SEQ ID NO: 6:

( i ) SEQUENCE CHARACTERISTICS:
        ( A ) LENGTH: 12
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 6:

Ser Ala Asn Tyr Phe Asp Ser Glu Val Ala Pro Arg
1               5                   10

( 2 ) INFORMATION FOR SEQ ID NO: 7:

( i ) SEQUENCE CHARACTERISTICS:
        ( A ) LENGTH: 8
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 7:

Asp His Asn Ile Glu Leu Ser Lys
1               5

( 2 ) INFORMATION FOR SEQ ID NO: 8:

( i ) SEQUENCE CHARACTERISTICS:
        ( A ) LENGTH: 9
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 8:

Ala His Asp Asp Pro Val Ala Leu Lys
1               5

( 2 ) INFORMATION FOR SEQ ID NO: 9:

( i ) SEQUENCE CHARACTERISTICS:
        ( A ) LENGTH: 13
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 9:

Phe Phe His Thr Gly Thr Asp Ala Glu Asp Ala Gly Asp
1               5                   10

( 2 ) INFORMATION FOR SEQ ID NO: 10:

( i ) SEQUENCE CHARACTERISTICS:
        ( A ) LENGTH: 12
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 10:

Ala Asn Glu Asn Ser Leu Leu Ser Ala Gln Leu Lys
1               5                   10

( 2 ) INFORMATION FOR SEQ ID NO: 11:

( i ) SEQUENCE CHARACTERISTICS:
        ( A ) LENGTH: 14
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 11:

Val Thr Ser Thr Glu Glu Tyr Pro His Leu Lys Pro Ala Xaa
1               5                   10

( 2 ) INFORMATION FOR SEQ ID NO: 12:

( i ) SEQUENCE CHARACTERISTICS:
        ( A ) LENGTH: 5

(B) TYPE: amino acid
(C) STRANDEDNESS: Not Relevant
(D) TOPOLOGY: Not Relevant (xi) SEQUENCE DESCRIPTION: SEQ ID NO: 12:

Asp Ile Trp Ser Lys
1               5

(2) INFORMATION FOR SEQ ID NO: 13:

(i) SEQUENCE CHARACTERISTICS:
    (A) LENGTH: 8
    (B) TYPE: amino acid
    (C) STRANDEDNESS: Not Relevant
    (D) TOPOLOGY: Not Relevant (xi) SEQUENCE DESCRIPTION: SEQ ID NO: 13:

Met Lys Gly Xaa Glu Asp Val Lys
1               5

(2) INFORMATION FOR SEQ ID NO: 14:

(i) SEQUENCE CHARACTERISTICS:
    (A) LENGTH: 6
    (B) TYPE: amino acid
    (C) STRANDEDNESS: Not Relevant
    (D) TOPOLOGY: Not Relevant (xi) SEQUENCE DESCRIPTION: SEQ ID NO: 14:

Met Gly Gln Thr Leu Pro
1               5

(2) INFORMATION FOR SEQ ID NO: 15:

(i) SEQUENCE CHARACTERISTICS:
    (A) LENGTH: 14
    (B) TYPE: amino acid
    (C) STRANDEDNESS: Not Relevant
    (D) TOPOLOGY: Not Relevant (xi) SEQUENCE DESCRIPTION: SEQ ID NO: 15:

Ser Ser Glu Ser Ile Pro His Leu Thr Ala Asp Ala Gly Leu
1               5                   10

(2) INFORMATION FOR SEQ ID NO: 16:

(i) SEQUENCE CHARACTERISTICS:
    (A) LENGTH: 13
    (B) TYPE: amino acid
    (C) STRANDEDNESS: Not Relevant
    (D) TOPOLOGY: Not Relevant (xi) SEQUENCE DESCRIPTION: SEQ ID NO: 16:

Tyr Ile Leu Val Asp Ile Asp Asp Ile Phe Val Gly Lys
1               5                   10

(2) INFORMATION FOR SEQ ID NO: 17:

(i) SEQUENCE CHARACTERISTICS:
    (A) LENGTH: 20
    (B) TYPE: nucleic acid
    (C) STRANDEDNESS: single
    (D) TOPOLOGY: linear (xi) SEQUENCE DESCRIPTION: SEQ ID NO: 17:

CTGTGGTGCC TGTTTTCTGG                                    20

(2) INFORMATION FOR SEQ ID NO: 18:

( i ) SEQUENCE CHARACTERISTICS:
    ( A ) LENGTH: 29
    ( B ) TYPE: nucleic acid
    ( C ) STRANDEDNESS: single
    ( D ) TOPOLOGY: linear ( x i ) SEQUENCE DESCRIPTION: SEQ ID NO: 18:

GGTGTCGACA CTCGAGCCCT CGGCAGATG                                    29

( 2 ) INFORMATION FOR SEQ ID NO: 19:

( i ) SEQUENCE CHARACTERISTICS:
    ( A ) LENGTH: 30
    ( B ) TYPE: nucleic acid
    ( C ) STRANDEDNESS: single
    ( D ) TOPOLOGY: linear ( x i ) SEQUENCE DESCRIPTION: SEQ ID NO: 19:

GGCGTCGACC AAGCGTTCTG GCTGGCTGTG                                   30